US012559525B2

(12) United States Patent
Vogel et al.

(10) Patent No.: US 12,559,525 B2
(45) Date of Patent: Feb. 24, 2026

(54) CONJUGATED FIBRONECTIN-BINDING PEPTIDES FOR USE IN TUMOR OR FIBROSIS DIAGNOSIS AND THERAPY

(71) Applicants: ETH Zürich, Zürich (CH); Paul Scherrer Institut

(72) Inventors: Viola Vogel, Zürich (CH); Mamta Chabria, Zürich (CH); Giulia Valpreda, Forschungsstrasse (CH); Belinda Trachsel, Forschungsstrasse (CH); Martin Behe, Forschungsstrasse (CH)

(73) Assignee: ETH Zürich, Zürich (CH)

( * ) Notice: Subject to any disclaimer, the term of this patent is extended or adjusted under 35 U.S.C. 154(b) by 632 days.

(21) Appl. No.: 17/938,092

(22) Filed: Oct. 5, 2022

(65) Prior Publication Data

US 2023/0212228 A1     Jul. 6, 2023

Related U.S. Application Data

(63) Continuation of application No. PCT/EP2021/025388, filed on Oct. 5, 2021.

(51) Int. Cl.
| | |
|---|---|
| *C07K 14/00* | (2006.01) |
| *A61P 11/00* | (2006.01) |
| *A61P 35/00* | (2006.01) |
| *G01N 33/68* | (2006.01) |

(52) U.S. Cl.
CPC ............ *C07K 14/001* (2013.01); *A61P 11/00* (2018.01); *A61P 35/00* (2018.01); *G01N 33/68* (2013.01)

(58) Field of Classification Search
CPC ........ C07K 14/00; C07K 14/31; C07K 14/78; A61P 35/00; A61P 11/00; A61P 37/00
See application file for complete search history.

(56) References Cited

FOREIGN PATENT DOCUMENTS

WO     WO2017216223 A1    12/2017

OTHER PUBLICATIONS

Bernhard, Petri; European International Search Report and Written Opinion for PCT/EP2021/025388; dated Jun. 9, 2022; 16 pages.
Arnoldini, Simon et al.; "Novel peptide probes to access the tensional state of fibronectin fibers in cancer"; Nature Communications, vol. 8, No. 1; Nov. 27, 2017; URL:http://www.nature.com/articles/s41467-017-01846-0>; 13 pages.
Hertig, Samuel et al.; "Engineering Mechanosensitive Multivalent Receptor-Ligand Interactions: Why the Nanolinker Regions of Bacterial Adhesins Matter"; Nano Letters; vol. 12, No. 10; Sep. 14, 2012; p. 5162-5168.
Vogel, Viola; "Unraveling the Mechanobiology of Extracellular Matrix"; Annual Review of Physiology; vol. 80, No. 1; Feb. 10, 2018; p. 353-387.
Post-Filed Experimental Data in Support of European Patent Application No. 17 731 525.6; dated Oct. 13, 2020; 6 pages.

*Primary Examiner* — Elly-Gerald Stoica
(74) *Attorney, Agent, or Firm* — Daniel A. Thomson; Emerson, Thomson and Bennett, LLC

(57) ABSTRACT

The present invention relates to fibronectin-binding peptides according to the sequence
FnI5BS-L1-FnI4BS-L2-FnI3BS-L3-FnI2BS
which are useful in tumor or fibrosis diagnosis and therapy. Instant peptides show improved fibronectin-binding and biodistribution properties compared to the prior art. Furthermore, instant peptides may be conjugated to a payload and are useful in the treatment and/or prevention of diseases associated with pathological fibronectin accumulation, including cancer and fibrosis. Instant peptides are also useful in diagnosis of diseases associated with pathological fibronectin accumulation, including cancer and fibrosis.

20 Claims, 6 Drawing Sheets

Specification includes a Sequence Listing.

2.7 Bq/Voxel

0 female Balb/c nude

Start of therapy:d=0    n=4

- 1)Vehicle (5ml/kg) i.v.daily x 7d
- 2)PDC_1 (500nM/kg)(5ml/kg) i.v. daily x 7d
- 3)PDC_2 (250nM/kg)(5ml/kg) i.v. daily x 7d
- 4)PDC_3 (125nM/kg)(5ml/kd) i.v. daily x 7d
- 5)PDC_4 (70nM/kg)(5ml/kd) i.v. daily x 7d

CONJUGATED FIBRONECTIN-BINDING PEPTIDES FOR USE IN TUMOR OR FIBROSIS DIAGNOSIS AND THERAPY

CROSS-REFERENCE TO RELATED APPLICATIONS

This application is a continuation of and claims priority to PCT application No. PCT/EP2021/025388, filed on Oct. 5, 2021. The entire contents of which is incorporated herein by reference.

FIELD OF THE INVENTION

The present invention relates to fibronectin-binding peptides for use in tumor or fibrosis diagnosis and therapy. Instant peptides show improved fibronectin-binding and biodistribution properties compared to the prior art. Furthermore, instant peptides may be conjugated to a payload and are useful in the treatment and/or prevention of diseases associated with pathological fibronectin accumulation, including cancer and fibrosis. Instant peptides are also useful in diagnosis of diseases associated with pathological fibronectin accumulation, including cancer and fibrosis.

BACKGROUND

Fibronectin (Fn) is a high-molecular weight (~440 kDa) glycoprotein of the extracellular matrix (ECM) that binds to membrane-spanning receptor proteins called integrins (Hynes, R. O. (2009), Science 326(5957): 1216-1219). Similar to integrins, fibronectin binds among other binding partners extracellular matrix (ECM) components such as collagen, fibrin, and heparan sulfate proteoglycans. Fibronectin exists as a protein dimer, consisting of two nearly identical monomers linked by a pair of disulfide bonds. The fibronectin protein is produced from a single gene, but alternative splicing of its pre-mRNA leads to the creation of several isoforms. Soluble plasma fibronectin is a major protein component of blood plasma that is produced by hepatocytes and circulates in body fluids at high concentrations of about 300 µg/mL. Insoluble cellular fibronectin is a major component of the ECM. It is secreted by various cells, primarily fibroblasts, as a soluble protein dimer and is then assembled into an insoluble matrix in a complex cell-mediated process.

Fibronectin plays a major role in cell adhesion, growth, migration and differentiation, and it is important for processes such as wound healing and embryonic development.

Altered fibronectin expression, degradation and organization has been associated with a number of pathologies, including cancer and fibrosis. Several of the morphological changes observed in tumors and tumor-derived cell lines have been attributed to altered fibronectin expression, increased fibronectin degradation and/or altered expression of fibronectin-binding receptors, such as different integrin types ($\alpha5\beta1$, $\alpha v\beta1$, $\alpha v\beta3$, $\alpha v\beta5$, $\alpha v\beta6$ or $\alpha v\beta8$ integrins).

In lung carcinoma fibronectin expression is increased, especially in non-small cell lung carcinoma. The adhesion of lung carcinoma cells to fibronectin enhances tumorigenicity and confers resistance to apoptosis-inducing chemotherapeutic agents. Fibronectin has been shown to stimulate the gonadal steroids that interact with vertebrate androgen receptors, which are capable of controlling the expression of cyclin D and related genes involved in cell cycle control. These observations suggest that fibronectin may promote lung tumor growth/survival and resistance to therapy, and it could represent a target for the development of new anti-cancer drugs. Fibronectin acts as a potential biomarker for radioresistance. FN-FGFR1 fusion is frequent in phosphaturic mesenchymal tumors.

WO2007/128563A1 teaches fusion proteins comprising an antibody or functional fragment thereof specifically binding the extracellular domain of oncofetal fibronectin (ED-B) and a specific effector selected from the cytokines IL-10, IL-15, IL-24 and GM-CSF (Granulocyte-macrophage colony-stimulating factor) for the manufacture of a medicament for treating tumors or chronic inflammatory diseases, in particular atherosclerosis, arthritis and psoriasis. ED-B is a 91-amino-acid type Ill homology domain that is inserted into the fibronectin molecule by a mechanism of alternative splicing at the level of the primary transcript whenever tissue remodeling takes place [Zardi et al., Embo J. 6(8): 2337-42 (1987)]. ED-B is essentially undetectable in healthy adult tissues. Its expression is strongly associated with the remodeling of the ECM and angiogenesis. The domain is abundant in many aggressive tumors and, depending on the tumor type, displays either predominantly vascular or diffuse stromal patterns of expression [Carnemolla et al., J. Cell Biol. 108(3): 1139-48 (1989)].

Compared to peptides, nanoparticles and antibodies for targeting live biological targets have a major setback when it comes to their permeability and retention at the target tissue (see Wilhelm et al, Analysis of nanoparticle delivery to tumours, Nature Reviews Materials 1, (2016) 1-12).

Antibodies are large proteins with a molecular weight of 150 kDa and a hydrodynamic radius of 15 to 20 nm. Moreover, antibodies and fragments thereof are relatively sensitive to environmental and metabolic challenges. Smaller fragments of antibodies such as monomers and the dimers of the Fab recognition patterns still represent bulky molecules with sizes of around 50 to 100 kDa, respectively. Smaller targeting compounds include proteins, peptides, nucleic acid-based ligands, e.g. aptamers, and small molecules [Bertrand et al., Advanced Drug Delivery Reviews 66, (2014): 2-25]. These smaller molecules have the advantage of a faster diffusion and faster targeting of the target tissue resulting in more homologous distribution within a pathological tissue like cancer or fibrosis.

However, one major and generally accepted drawback of therapeutic peptides is their poor stability in blood plasma leading to a short half-life time and, consequently, reduced therapeutic or diagnostic efficacy. Rapid degradation of peptides in blood serum is often observed to result in a loss of affinity to the target protein. Therefore, strategies for stabilization have to be introduced. There are natural peptides mainly originating from amphibians and reptiles, which show a higher metabolic stability in human blood than the related human analogues due to evolutionary engineering. Another possibility to increase stability is chemically by changing the metabolic cutting sites within a peptide. This includes the replacement of natural amino acids by unnatural amino acids or a chemical modification of the amide bonds.

In the context of bacterial wound infection, Chabria et al. (Nature Communications, 1:135, 2010, 1-9) report that specific binding of bacterial FnBR via backbone hydrogen bonds can be mechanically regulated by "stretching" Fn-fibers in vitro and suggest that cell-generated forces are sufficiently high to deactivate specific binding of bacterial adhesins to Fn-fibers. The authors thus speculate that the mechanobiology of the Fn-comprising ECM might regulate bacterial and cell-binding events, virulence and the course of infection.

Cao et al. [PNAS, vol. 109, 19:7251-7256, May 8, 2015] report phage display-based molecular probes LNLPHG and RFSAFY that discriminate force-induced structural states of fibrillar fibronectin in vivo, a so-called "relaxed" (preferentially bound by LN LPHG) and a "strained" (preferentially bound by RFSAFY) state of Fn fibers. Phages displaying SRWYRI, ARERFY and GSNSKY preferentially also bound the relaxed state with lower but significant binding affinity. Random phage displayed-peptide probes exhibited strain-selective binding to manually extruded fibronectin (Fn) fibers, cell-derived Fn ECM and ex vivo living lung slices. The authors speculate on the possible future use of these peptide probes for mapping molecular strain events in unmodified native ECM microenvironments as well as for targeting Fn (ECM) in altered structural states associated with disease. On the other hand, the authors admit that there still is no direct evidence that extensibility of Fn within fibers and Fn type Ill domain unfolding events observed under artificial strain conditions actually occur in vivo. Hence, it is highly speculative whether or not peptides identifying either the "relaxed" or "strained" Fn could function as tumor markers, in particular, because only the phages displaying those peptides were tested, but not the peptides alone. Hertig et al. (Nano Lett., 12, 5132-5168, 2012) disclose the isolation and further engineering of bacterially derived Fn-binding proteins (FnBPs). The natural FnBPs are covalently linked to the bacterial cell membrane and can contain several intrinsically disordered Fn-binding repeats (FnBRs). Interestingly, the FnBRs expressed by several gram-positive bacteria and a spirochete show little homology, though they all recognize and bind the same domains of Fn. Conserved residues are mostly found in the FnI-binding motifs, with the E-D/E-T/S motif being highly conserved and found in almost every FnBR. Fn features five FnI modules, which are spaced apart by peptide linkers and all of which can serve as FnBP binding partners.

In summary, fibronectin is a prevalent protein in the plasma and ECM of tissues, which can be upregulated in fibrosis and cancer tissues. Splice variants of fibronectin have utility for targeting splice variant-specific cancer types. The binding of naturally occurring and phage-display-based FnBPs can vary with the natural relaxed and the artificially strained state of Fn (S. Arnoldini, A. Moscaroli, M. Chabria, M. Hilbert, S. Hertig, R. Schibli, M. Béhé, and V. Vogel, "Novel peptide probes to assess the tensional state of fibronectin fibers in cancer.," *Nat Commun*, vol. 8, no. 1, p. 1793, November 2017; C. M. Fonta, S. Arnoldini, D. Jaramillo, A. Moscaroli, A. Oxenius, M. Béhé, and V. Vogel, "Fibronectin fibers are highly tensed in healthy organs in contrast to tumors and virus-infected lymph nodes.," *Matrix Biology Plus*, vol. 8, p. 100046, November 2020).

The document WO 2017/216223 further teaches compositions comprising fibronectin-binding peptides linked to a diagnostic or therapeutic agent.

SUMMARY OF THE INVENTION

It was an object of the present invention to provide novel fibronectin-binding peptide sequences, with improved affinity for fibronectin, in particular for Fib1 construct, and with improved biodistribution properties.

The object is achieved by the embodiments described herein and as characterized by the claims.

The present inventors have found that FnBPA5.1 sequence, which is derived from the FnBPA5 sequence (SEQ ID NO: 13) upon three amino acid substitutions and two deletions, shows surprisingly improved affinity for Fib1, as measured in the fluorescence polarization assay (Example 1, FIG. 1). The present inventors have further studied the biodistribution of the fibronectin-binding peptides of the present invention and have surprisingly found that FnBPA5.1 sequence with a radioisotope label has improved uptake in tumors in comparison to the FnBPA5 sequence as known from the prior art, as demonstrated in the experiments with PC3 xenograft mice (Example 4, FIG. 4 and Example 6 and 7, FIG. 6), as well as studies in 67NR orthotopic and syngeneic breast tumor mice (Example 5, FIG. 5, and Examples 8 and 9, FIG. 7). It has been further surprisingly established that at the same time the fibronectin binding peptide of the present invention demonstrate lower uptake in spleen and liver in comparison to the FnBPA5 sequence as known from the prior art, which as known to the skilled person is a desired feature from the biodistribution point of view.

The invention will be summarized in the following embodiments.

In a first embodiment, the present invention relates to a fibronectin binding peptide comprising the sequence: FnI5BS-L1-FnI4BS-L2-FnI3BS-L3-FnI2BS wherein:

FnI5BS is a polypeptide sequence selected from

```
                              (SEQ ID NO.: 1)
      Gln-Val-Thr-Thr-Gly-Ser-Asn, (SEQ ID NO.: 2)
      Gln-Val-Thr-Thr-Ala-Ser-Asn, (SEQ ID NO.: 3)
      Gln-Val-Thr-Thr-Val-Ser-Asn,
      and (SEQ ID NO.: 4)
      Gln-Val-Thr-Thr-Ser-Ser-Asn;
```

FnI4BS is a polypeptide sequence selected from

```
                              (SEQ ID NO.: 5)
      Val-Glu-Phe-Thr-Glu-Glu-Ser, (SEQ ID NO.: 6)
      Val-Glu-Phe-Ser-Glu-Glu-Ser, (SEQ ID NO.: 7)
      Val-Glu-Phe-Cys-Glu-Glu-Ser, (SEQ ID NO.: 8)
      Val-Glu-Phe-Asn-Glu-Glu-Ser,
      and (SEQ ID NO.: 9)
      Val-Glu-Phe-Gln-Glu-Glu-Ser;
```

FnI3BS is a polypeptide of sequence Gly-Ile-Val-Thr-Gly-Ala-Val (SEQ ID NO: 10);

FnI2BS is a polypeptide of sequence His-Thr-Thr-Val-Glu-Asp-Thr (SEQ ID NO: 11); and L1, L2 and L3 are each a polypeptide sequence comprising 0, 1 or 2 amino acid residues.

In a particular embodiment, the present invention relates to the fibronectin binding peptide of the present invention, wherein FnI5BS is a polypeptide of sequence according to SEQ ID NO: 1; and/or FnI4BS is a polypeptide of sequence according to SEQ ID NO: 5.

In a further particular embodiment, the present invention relates to the fibronectin binding peptide of the present invention, wherein FnI5BS is a polypeptide of sequence according to SEQ ID NO: 1; and FnI4BS is a polypeptide of sequence according to SEQ ID NO: 5.

In again a further particular embodiment the present invention relates to the fibronectin binding peptide of the present invention, wherein L1 is a single amino acid residue Leu; and/or L2 is a single amino acid residue selected from Leu, Ile, Val, Ala and Met, preferably Leu; and/or L3 is a dipeptide of sequence Ser-Asp.

In again a further particular embodiment the present invention relates to the fibronectin binding peptide of the present invention, wherein L1 is a single amino acid residue Leu; and L2 is a single amino acid residue Leu; and L3 is a dipeptide of sequence Ser-Asp.

In again a further particular embodiment the present invention relates to the fibronectin binding peptide of the present invention, comprising a polypeptide sequence Gln-Val-Thr-Thr-Gly-Ser-Asn-Leu-Val-Glu-Phe-Thr-Glu-Glu-Ser-Leu-Gly-Ie-Val-Thr-Gly-Ala-Val-Ser-Asp-His-Thr-Thr-Val-Glu-Asp-Thr (SEQ ID NO: 12).

In again a further particular embodiment the present invention relates to the fibronectin binding peptide of the present invention, having a polypeptide sequence according to SEQ ID NO: 12.

In again a further particular embodiment the present invention relates to the fibronectin binding peptide of the present invention, characterized by binding to Fib1 (SEQ ID NO: 14) with a $K_D$ of 5.0 nM or tighter, as preferably determined by using a fluorescence polarization assay.

In again a further particular embodiment the present invention relates to the fibronectin binding peptide of the present invention, further conjugated to a payload.

In again a further particular embodiment the present invention relates to the fibronectin binding peptide of the present invention, wherein the payload is directly conjugated to the N or C terminus of the said polypeptide sequence through an amide bond, or wherein the payload is conjugated to the N or C terminus of the said polypeptide sequence via a linker.

In again a further particular embodiment the present invention relates to the fibronectin binding peptide of the present invention, wherein the linker comprises a peptide moiety, a PEG moiety, a moiety derived from cadaverine or a $C_{1-12}$ alkylene moiety.

In again a further particular embodiment the present invention relates to the fibronectin binding peptide of the present invention, wherein the payload is a biologically active molecule (BAM) or an imaging agent.

In again a further particular embodiment the present invention relates to the fibronectin binding peptide of the present invention, wherein the payload is a biologically active molecule (BAM).

In again a further particular embodiment the present invention relates to the fibronectin binding peptide of the present invention, wherein the biologically active molecule is selected from the group consisting of cytostatic agent, cytotoxic agent, cytokine, transcription factor inhibitor, proteasome and protease inhibitor, apoptosis modulator, cell cycle modulator, angiogenesis inhibitor, hormone or hormone derivative, photodynamic therapy molecule, nano- and microparticle for thermoablation therapy, radionuclide, miRNA, siRNA and immunomodulatory antigen molecule.

In again a further particular embodiment the present invention relates to the fibronectin binding peptide of the present invention, wherein the biologically active molecule is selected from the group consisting of Paclitaxel, Chlorambucil, Endostatin, Sunitinib, Interleukin-7, $^{177}$Lu, and $^{111}$In.

In again a further particular embodiment the present invention relates to the fibronectin binding peptide of the present invention, wherein the payload is an imaging agent.

In again a further particular embodiment the present invention relates to the fibronectin binding peptide of the present invention, wherein the imaging agent comprises a radionuclide, a fluorescent dye, a chemiluminescent agent, a bioluminescent agent, a spectrally resolvable inorganic fluorescent semiconductor nanocrystal, a metal nanoparticle, a nanocluster, a paramagnetic metal ion, an enzyme, a colorimetric label, biotin, dioxigenin, a hapten or a protein.

In again a further particular embodiment the present invention relates to the fibronectin binding peptide of the present invention, wherein the imaging agent is selected from the group consisting of radionuclide, MRI active compound, ultrasound contrast agent, fluorophore, marker for PET and SPECT, preferably selected from $^{44}$Sc, $^{64}$Cu, $^{67/68}$Ga, $^{99m}$Tc, $^{111}$In, fluorophore in the far red/near-IR spectral region, and Gd-based and Fe-oxide particle based MRI contrast agent.

In again a further particular embodiment the present invention relates to the fibronectin binding peptide of the present invention, wherein the imaging agent is selected from $^{68}$Ga, $^{99m}$Tc, $^{111}$In, $^{44}$Sc and $^{64}$Cu.

In again a further particular embodiment the present invention relates to the fibronectin binding peptide of the present invention, wherein the payload comprises a radionuclide, preferably selected from $^{67}$Cu, $^{90}$Y, $^{111}$In, $^{131}$I, $^{161}$Tb, $^{169}$Er and $^{177}$Lu or preferably selected from $^{44}$Sc, $^{64}$Cu, $^{67/68}$Ga $^{99m}$Tc, and $^{111}$In.

In again a further particular embodiment the present invention relates to the fibronectin binding peptide of the present invention, wherein the payload is [$^{111}$In]In-NODAGA moiety.

In a further embodiment, the present invention relates to a pharmaceutical composition comprising the fibronectin binding peptide as described herein and a pharmaceutically acceptable carrier.

In again a further embodiment, the present invention relates to the fibronectin binding peptide of the present invention or the pharmaceutical composition of the present invention for use in therapy.

In again a further embodiment, the present invention relates to the fibronectin binding peptide of the present invention, or the pharmaceutical composition of the present invention for use in the treatment or prevention of a disease associated with pathologic fibronectin accumulation.

In a particular embodiment, the present invention relates to the fibronectin binding peptide for use of the present invention or the pharmaceutical composition for use of the present invention, wherein the disease associated with pathologic fibronectin accumulation is selected from the group consisting of fibrosis, cancer, lymphedema, immune disease, autoimmune disease, and atherosclerosis.

In a further particular embodiment, the present invention relates to the fibronectin binding peptide for use of the present invention or the pharmaceutical composition for use of the present invention, wherein the autoimmune diseases is selected from systemic sclerosis, diabetes type 1, Graves' disease, multiple sclerosis and rheumatoid arthritis.

In again a further particular embodiment, the present invention relates to the fibronectin binding peptide for use of the present invention or the pharmaceutical composition for use of the present invention, wherein the fibrosis is selected from pulmonary fibrosis, liver fibrosis, and kidney fibrosis.

In again a further particular embodiment, the present invention relates to the fibronectin binding peptide for use of the present invention or the pharmaceutical composition for use of the present invention, wherein the cancer is selected from breast cancer, head and neck squamous cell carcinoma, prostate cancer, renal cancer, pancreatic cancer and lung cancer.

In again a further particular embodiment, the present invention relates to the fibronectin binding peptide for use of the present invention or the pharmaceutical composition for use of the present invention, wherein the lung cancer is a non-small lung cell cancer.

In a further embodiment, the present invention relates to the fibronectin binding peptide of the present invention or the pharmaceutical composition of the present invention for use in diagnosis.

In a further embodiment, the present invention relates to the fibronectin binding peptide of the present invention or the pharmaceutical composition of the present invention for use in diagnosis of a disease associated with pathologic fibronectin accumulation.

In a particular embodiment, the present invention relates to the fibronectin binding peptide for use or the pharmaceutical composition for use of the present invention, wherein the disease associated with pathologic fibronectin accumulation is selected from the group consisting of fibrosis, cancer, lymphedema, immune disease, autoimmune disease, and atherosclerosis.

In a further particular embodiment, the present invention relates to the fibronectin binding peptide for use or the pharmaceutical composition for use of the present invention, wherein the autoimmune diseases is selected from systemic sclerosis, diabetes type 1, Graves' disease, multiple sclerosis and rheumatoid arthritis.

In again a further particular embodiment, the present invention relates to the fibronectin binding peptide for use or the pharmaceutical composition for use of the present invention, wherein the fibrosis is selected from pulmonary fibrosis, liver fibrosis, and kidney fibrosis.

In again a further particular embodiment, the present invention relates to the fibronectin binding peptide for use or the pharmaceutical composition for use of the present invention, wherein the cancer is selected from breast cancer, head and neck squamous cell carcinoma, prostate cancer, renal cancer, pancreatic cancer and lung cancer.

In again a further particular embodiment, the present invention relates to the fibronectin binding peptide for use or the pharmaceutical composition for use of the present invention, wherein the lung cancer is a non-small lung cell cancer.

DETAILED DESCRIPTION OF THE INVENTION

Figure 1:
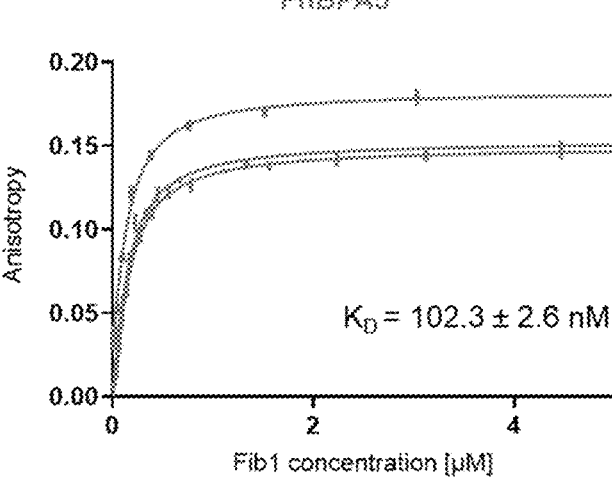
FIG. 1: Affinity measurements of Cy5-labelled FnBPA5.1 and FnBPA5 towards the N-terminal 30 kDa fragment of Fibronectin (Fib1) according to SEQ ID NO: 14. Curves display triplicates measurements of fluorescence polarization. Error bars display standard deviations. Analysis was conducted using GraphPad Prism. $K_D$ is shown in nM.
Figure 1:
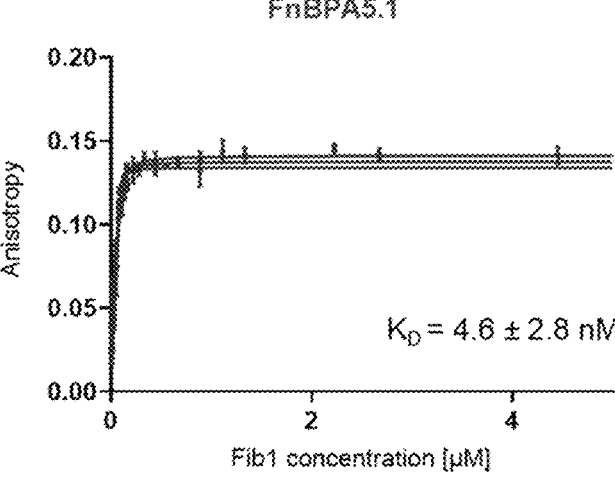

The invention is described in detail in the following embodiments. It is to be understood that all the combinations of features as disclosed herein are envisaged.

Fibronectin-Binding Peptides

In a first embodiment, the present invention relates to a fibronectin binding peptide comprising the sequence:

FnI5BS-L1-FnI4BS-L2-FnI3BS-L3-FnI2BS.

FnI5BS as defined herein refers to FnI5 binding sequence, which according to the present invention is a polypeptide sequence selected from

```
                                    (SEQ ID NO.: 1)
        Gln-Val-Thr-Thr-Gly-Ser-Asn, (SEQ ID NO.: 2)
        Gln-Val-Thr-Thr-Ala-Ser-Asn, (SEQ ID NO.: 3)
        Gln-Val-Thr-Thr-Val-Ser-Asn,
        and (SEQ ID NO.: 4)
        Gln-Val-Thr-Thr-Ser-Ser-Asn.
```

Preferably, FnI5BS is a polypeptide of sequence according to SEQ ID NO: 1.

FnI4BS as defined herein refers to FnI4 binding sequence, which according to the present invention is a polypeptide sequence selected from

```
                                    (SEQ ID NO.: 5)
        Val-Glu-Phe-Thr-Glu-Glu-Ser, (SEQ ID NO.: 6)
        Val-Glu-Phe-Ser-Glu-Glu-Ser, (SEQ ID NO.: 7)
        Val-Glu-Phe-Cys-Glu-Glu-Ser, (SEQ ID NO.: 8)
        Val-Glu-Phe-Asn-Glu-Glu-Ser,
```

-continued and (SEQ ID NO.: 9)

Val-Glu-Phe-Gln-Glu-Glu-Ser;

Preferably, FnI4BS is a polypeptide of sequence according to SEQ ID NO: 5.

Thus preferably, the present invention relates to an embodiment wherein FnI5BS is a polypeptide of sequence according to SEQ ID NO: 1; and/or FnI4BS is a polypeptide of sequence according to SEQ ID NO: 5. In a further preferred embodiment, FnI5BS is a polypeptide of sequence according to SEQ ID NO: 1; and FnI4BS is a polypeptide of sequence according to SEQ ID NO: 5.

As defined herein, FnI3BS, which refers to a FnI3 binding sequence, is a polypeptide of sequence Gly-Ile-Val-Thr-Gly-Ala-Val (SEQ ID NO: 10).

As further defined herein, FnI2BS which refers to FnI2 binding sequence, is a polypeptide of sequence (His-Thr-Thr-Val-Glu-Asp-Thr (SEQ ID NO: 11).

L1, L2 and L3 are each a polypeptide sequence comprising 0, 1 or 2 amino acid residues. L1, L2 and L3 are linkers connecting FnI5 binding sequence (FnI5BS) and FnI4 binding sequence (FnI4BS), FnI4 binding sequence (FnI4BS) and FnI3 binding sequence (FnI3BS), and FnI3 binding sequence (FnI3BS) and FnI2 binding sequence (FnI2BS), respectively. At the same time, L1, L2 and L3 preferably do not necessarily contribute to the binding affinity through direct interactions with the residues of fibronectin.

Thus, L1 is polypeptide sequence comprising 0, 1 or 2 amino acid residues. Preferably, L1 is a single amino acid residue Leu.

L2 is polypeptide sequence comprising 0, 1 or 2 amino acid residues. Preferably L2 is a single amino acid residue selected from Leu, lie, Val, Ala and Met. More preferably, L2 is Leu.

L3 is polypeptide sequence comprising 0, 1 or 2 amino acid residues. Preferably L3 is a dipeptide of sequence Ser-Asp.

Most preferably, in the embodiments of the present invention, L1 is a single amino acid residue Leu; and L2 is a single amino acid residue Leu; and L3 is a dipeptide of sequence Ser-Asp.

Preferably, the fibronectin binding peptide of the present invention, comprises a polypeptide sequence Gln-Val-Thr-Thr-Gly-Ser-Asn-Leu-Val-Glu-Phe-Thr-Glu-Glu-Ser-Leu-Gly-Ie-Val-Thr-Gly-Ala-Val-Ser-Asp-His-Thr-Thr-Val-Glu-Asp-Thr (SEQ ID NO: 12). More preferably, the fibronectin binding peptide of the present invention has a polypeptide sequence according to SEQ ID NO: 12.

The preferred sequence of FnBPA5.1 (SEQ Id NO: 12) of the present invention differs from FnBPA5 sequence (SEQ ID NO: 13) of the prior art in that:

Glu residue at position 5 in the sequence of FnBPA5 known from the prior art (SEQ ID: 13), (which corresponds to the position 5 of FnI5BS sequence—SEQ ID NO: 1), is replaced with glycine;

Asp residue at position 12 of the prior art sequence of FnBPA5 (SEQ ID NO: 13) (which corresponds to the position 4 of FnI4BS sequence—SEQ ID NO: 5) is replaced with a Thr residue;

Thr residue at position 16 of the prior art sequence of FnBPA5 (SEQ ID NO:13) (which corresponds to the first residue of L2) is replaced with Leu;

Lys residue at the position 17 and Lys residue at the position 34 the prior art sequence of FnBPA5 (SEQ ID NO: 13) are deleted.

The present inventors have surprisingly found that the resulting peptide sequence, herein referred to as FnBPA5.1 sequence (SEQ ID NO: 12) shows improved affinity for Fib1, improved uptake in tumors and lower uptake in spleen and liver. It is noted that it is conceivable to the skilled person that similar substitutions at the same position are likely to result with the same effect on affinity for Fib1, and/or lead to improved uptake in tumors and lower uptake in spleen and liver, as described herein. Therefore, the present invention also encompasses the embodiments wherein the Glu residue at position 5 of FnBPA5 sequence (SEQ ID NO: 13) has been replaced with residues with similar properties to glycine, for example with a residue selected from Ala, Val and Ser. The resulting FnI5 binding sequences, also referred to as FnI5BS, are selected from SEQ ID NO: 2 to 4. The present invention further encompasses the embodiments, wherein the Asp residue at position 12 of the prior art sequence of FnBPA5 (SEQ ID NO: 13) has been replaced with residues with similar properties to Thr, for example with a residue selected from Ser, Cys, Asn and Gln. The resulting FnI5 binding sequences, also referred to as FnI4BS, are selected from SEQ ID NO: 6 to 9. It is further conceivable to the skilled person that Thr residue at position 16 of the prior art sequence of FnBPA5 (SEQ ID NO:13) may be replaced with a residue similar in properties to Leu, for example a residue selected from Ile, Val, Ala and Met.

The present invention encompasses fibronectin binding peptides as described herein, which bind to fibronectin, in particular which bind to Fib1. Preferably, the fibronectin binding peptide of the present invention as defined herein binds to fibronectin, preferably to Fib1, with an affinity better than that measured for a peptide according to SEQ ID NO:13, which is also referred to as FnBPA5 peptide known from the prior art. As indicated in FIG. 1, the said affinity of FnBPA5 peptide to Fib1 corresponds to $K_D$=102.3 nM.

Preferably, said affinity is measurable by using a fluorescence anisotropy assay, using a peptide with N-terminally appended Cy5 label (as described in Preparative Example 1). Detailed protocol for the measurement is included in Example 1.

Thus, in a preferred embodiment the fibronectin binding peptide of the present invention is characterized by binding to Fib1 (construct according to SEQ ID NO: 14) with a $K_D$ of 100 nM or tighter, 50 nM or tighter, 25 nM or tighter, 10 nM or tighter, 5.0 nM or tighter, as preferably determined by using a fluorescence anisotropy assay as described herein. The term "or tighter" refers preferably to higher affinities, which can be expressed by lower $K_D$ values.

Fibronectin-Binding Peptide-Payload Conjugates

In a further embodiment, the present invention relates to the fibronectin binding peptide of the present invention, as described hereinabove, further conjugated to a payload. In other words, the fibronectin binding peptide of the present invention is in certain embodiments linked to a payload.

According to the present invention, there is no specific restriction as to how the fibronectin binding peptide and the payload are linked to each other, as long as the fibronectin binding peptide and the payload are linked in a manner that is sufficiently stable under physiological conditions, preferably in blood plasma, to physically and/or chemically connect/allocate/bind the components together until they reach the target site. The fibronectin binding peptide and the payload may be linked to each other covalently or non-covalently, e.g. by hydrophobic interaction, van der Waals forces, electrostatic attraction, etc. or via one or more spacers or at least one linker. The said linker in certain embodiments may be a cleavable linker. The expression "cleavable linker" means any linker which can be cleaved physically or chemically. Examples for physical cleavage are cleavage by light, radioactive emission or heat, while examples for chemical cleavage include cleavage by redox-reactions, hydrolysis, pH-dependent cleavage or cleavage by enzymes.

As understood herein, the payload moiety can be directly conjugated to any amino acid residue within the fibronectin binding peptide of the invention (or to any suitable chemical group therein), using any chemical coupling known in the art or described herein suitable for the conjugation of the payload moiety preferably to an amino acid residue (e.g., an amino acid side chain). Accordingly, said coupling may result in one or more chemical groups spaced between the payload moiety and the amino acid (e.g., amino acid side chain) of the fibronectin-binding peptide of the invention, which groups form as a result of the coupling reaction, as known in the art.

Alternatively, as described herein, the payload moiety may be conjugated to any amino acid residue within the fibronectin binding peptide of the invention indirectly, that is, via a linker group. In such embodiments, the payload is conjugated to a linker group, which linker group is conjugated to an amino acid residue within the fibronectin binding peptide of the invention. The conjugation between the payload and the linker group and between the linker group and an amino acid residue or chemical group of the fibronectin binding peptide of the invention may be any conjugation method and/or compound suitable for effecting such conjugation as described herein or as otherwise known in the art.

The conjugation of the payload moiety may be directed to any amino acid residue within the fibronectin binding peptide of the invention. Thus, the payload moiety may be directly or indirectly conjugated to an amino acid residue within the fibronectin binding peptide of the invention. Preferably, the payload moiety may be directly or indirectly conjugated to an amino acid residue that is at an N-terminal end or C-terminal end of the fibronectin binding peptide of the invention. Alternatively or additionally, the payload moiety may be directly or indirectly conjugated to an internal amino acid residue within the fibronectin binding peptide of the invention. As used throughout this disclosure, an internal residue or internal chemical group references an amino acid residue or chemical group of the fibronectin binding peptide of the invention that is not at the terminus of a peptide chain. As is known in the art, conjugation methods (whether direct or indirect) may require the chemical modification of one or both sites of conjugation (e.g., modification of an amino acid residue and/or modification of the payload moiety). Accordingly, the present invention also encompasses chemical modification of the fibronectin binding peptide of the invention.

Preferably, the fibronectin binding peptide of the present invention relates to an embodiment, wherein the payload is directly conjugated to the N or C terminus of the said polypeptide sequence through an amide bond. Further preferably, the payload is directly conjugated to the N or C terminus of the said polypeptide sequence through an amide bond.

Alternatively, the payload may be conjugated to the N or C terminus of the said polypeptide sequence via a linker. Preferred linkers of the present invention comprise a moiety selected from a peptide moiety, a PEG moiety, a moiety derived from cadaverine and a $C_{1-12}$ alkylene moiety. Preferably, the linker comprises a peptide moiety. Preferably, the linker is the peptide moiety is of sequence Gly-Gly-Gly or of sequence Cys-Gly-Gly-Gly (SEQ ID NO: 15). As understood to the skilled person, the linker may be N-terminally acetylated.

The payload may preferably be conjugated to the linker via amide bond formation or maleimide-thiol conjugation.

The payload in the present invention is not particularly limited. In the preferred embodiment, the payload is a biologically active molecule (BAM) or an imaging agent.

In certain preferred embodiments of the present invention, the payload is a biologically active molecule (BAM).

Preferably, the biologically active molecule as encompassed by the present invention is selected from the group consisting of cytostatic agent, cytotoxic agent, cytokine, transcription factor inhibitor, proteasome and protease inhibitor, apoptosis modulator, cell cycle modulator, angiogenesis inhibitor, hormone or hormone derivative, photodynamic therapy molecule, nano- and microparticle for thermoablation therapy, radionuclide, miRNA, siRNA and immunomodulatory antigen molecule.

As understood herein, the preferably cytostatic agent is selected from Doxorubicin, Paclitaxel, Chlorambucil, Topotecan and Vincristine.

As further understood herein, preferably cytokine is selected from Interleukin-2, Interleukin-7, Interferon-γ and tumor necrosis factors. Further suitable cytokines for use as payload according to the present invention are, for example, interleukin 2, interleukin 7, interferon α-2α, interferon α-2b, interferon-Iα, interferon-Iβ, interferon γ-Iβ, tumor necrosis factor, and any derivatives thereof.

As further understood herein, transcription factor inhibitor is preferably selected from Curcumin, Ribavirin and Genistein. Further suitable transcription factor inhibitors for use as payload according to the present invention are, for example compounds that inhibit activation of NF-KB such as curcumin (diferuloylmethane) epigallocatechin-3-gallate (EGCG; green tea polyphenols), phenanthrolines, pyrrolinedithiocarba-mate (PDTC), quercetin, tepoxaline (5-(4-chlorophenyl)-N-hydroxy-(4-methoxyphenyl)-N-methyl-1H-pyrazole-3-propan-amide), PMC (2,2,5,7,8-pentamethyl-6-hydroxychromane), benzyisocyanate, resveratol, genistein, lupeol, lycopene, panepoxydone, epoxyquinomicin C, dehydroxymethylepoxy-quinomicin (DHMEQ), cycloepoxydon, gliotoxin, as well as 1-KB-alpha phosphorylation and/or degradation inhibitors such as PS-1,145, BAY-11-7082 (E3[(4-methylphenyl)-sulfonyl]-2-propenenitrile), BAY-11-7085 (E3[(4-t-butylphenyl)-sulfonyl]-2-propenenitrile), cycloepoxydon; 1-hydroxy-2-hydroxy-methyl-3-pent-1-enylbenzene, sanguinarine (pseudochelerythrine, 13-methyl-[I,3]-benzo-dioxolo-[5,6-c]-1,3-dioxolo-4,5 phenanthridinium), sulfasalazine, capsaicin (8-methyl-N-vanillyl-6-nonenamide), emodin (3-methyl-I,6,8-trihydroxy-anthraquinone), erbstatin (tyrosine kinase inhibitor), estrogen (E2), gliotoxin, genistein, resiniferatoxin, and miscellaneous inhibitors of NF-KB such as beta-amyloid protein, glucocorticoids (dexamethasone, prednisone, methylprednisolone), leptomycin B (LMB), O,O'-bismyristoyl thiamine disulfide (BMT), ADP ribosylation inhibitors, e.g., bi-, tri-, or tetracyclic lactames, 1,8-naphtalimide derivatives, phenanthridin-6-ones, 3,4-dihydro-5-methyl-isoquinolin-1(2H)-one, benzoxazole-4-carboxamide, 1,6-naphthyridine-5(6H)-ones, quinazolin[3,4-d]pyrimidin-4(3H)-ones, 1,5-dihydroxyisoquinoline, 2-methyl-quinazolin-4[3H]-ones, I,IIb-dihydro-[2H]benzo-pyrano [4,3,2-de]isoquinolin-3-one, atrial natriuretic peptide (ANP), atrovastatin (HMG-CoA reductase inhibitor), calcitriol (1a,25-dihydroxyvitamine D3), E3330 (quinone derivative), herbimycin A, hypericin, hydroquinone (HQ), KT-90

(morphine synthetic derivatives), mevinolin, 5'-methylthio-adenosine (MTA), pentoxifylline (1-(5'-oxohexyl)3,7-dim-ethylxanthine, PTX), phenyl-N-tert-butylnitrone (PBN), pituitary adenylate cyclase-activating polypeptide (PACAP), quinadril (ACE inhibitor), ribavirin, secretory leukocyte protease inhibitor (SLPI), serotonin derivative (N-(p-coumaroyl) serotonin, silymarin, vasoactive intestinal peptide (VIP), D609 (phosphatidylcholine-phospho-lipase C inhibitor), R031-8220 (PKG inhibitor), SB203580 (p38 MAPK inhibitor), triptolide (PG490, extract of Chinese herb), LY294,002, mesalamine, wortmannin (fungal metabolite), or CHS 828 (N-(6-(p-chlorophenoxy)-hexyl)-N'-cyano-N,-4-pyridylguanidine), sesquiterpene lactones such as parthenoilde, helenalin, miller-9E-enolid and bud-lein A.

As understood herein, proteasome and protease inhibitors are preferably selected from peptide aldehydes: ALLnL (N-acetyl-leucinyl-leucynil-norleucynal, MG101), LLM (N-acetyl-leucinyl-leucynil-methional), Z-LLnV (carboben-zoxyl-leucinyl-leucyni I-norvalinal, MG115), Z-LLL (car-bobenzoxyl-leucinyl-leucynil-leucynal, MG132), boronic acid derivatives, e.g. PS-273, PS-293, PS-296, PS-303, PS-305, PS-313, PS-321, PS-325, PS-334, PS-341, PS-364, PS-352, PS-383, lactacystine, beta-lactone, boronic acid peptide, ubiquitin ligase inhibitors deoxyspergualin, APNE (N-acetyl-DL-phenylalanine-beta-naphthylester), BTEE (N-benzoyl L-tyrosine-ethylester), DCIC (3,4-dichloroiso-coumarin), DFP (diisopropylfluorophosphate), TPCK (N-al-pha-tosyl-L-phenylalanine chloromethyl ketone), and TLCK (N-alpha-tosyl-L-lysine chloromethyl ketone).

As further understood herein, apoptosis modulator is preferably selected from Imatinib, Erlotinib and Bryostatin. Further suitable apoptosis modulators for use as payload according to the present invention are, for example, farnesyl transferase inhibitors, e.g. R115777, SCH66336, BMS214662, Imatinib, 17-AAG, EGFR inhibitors, e.g. ZD1839, ZD647, BIBW 2992, or erlotinib, MEK inhibitors, e.g. PD 032590, RAF inhibitors e.g. BAY43-9006, PKG inhibitors, e.g. UCN-01, PKC-412, Bryostatin, ISIS-3521, LY333531, safingol, CGP-41251 (midostaurin), HDAC inhibitors, e.g., suberoyl-3-aminopyridineamide hydroxamic acid, lonidamine, apoptin, survivin, rapamycin, CCI-779, RAD001 (everolimus), PXD101, tyrosine kinase inhibitors, e.g. Iressa, OSI-774, STI-571, inhibitors of enzymes in the mitogen-activated protein kinase pathway e.g., PD-098059, U-0126. Especially preferred cell cycle modulators for use according to the present invention are, for example, flavopiridol, bryostain-1, roscovitine, BMS-387032, perifosine, or lovastatin.

As further understood herein, preferably cell cycle modulator is selected from Flavopiridol and Roscovitine.

As further understood herein, angiogenesis inhibitor is preferably selected from Endostatin, Celexocib, ADH-1 (exherin) and Sunitinib. Further suitable angiogenesis inhibitors for use as payload according to the present invention are, for example thalidomide, endostatin, celecoxib, ABT-510, combrestatin A4, dalteparin, dimethyl-xanthe-none acetic acid, lenalidomide, LY317615 (enzastaurin), PPI-2458, ADH-1 (exherin), AG-013736, AMG-706, AZD2171, Bay 43-9006 (sorafenib), BMS-582664, CH IR-265, GW786034 (pazopanib), PI-88, PTK787/ZK 222584 (vatalanib), RAD001 (everolimus), SU 11248 (suni-tinib), suramin, XL184, ZD6474, ATN-161, or EMO 121974 (cilenigtide), and saposin-A derived peptides inducing thrombospondin-1 (preferably featuring Seq. ID Nos. 4 (DWLPK) and 5 (DWLP) of US Patent 2015/0320825 A1).

As further understood herein, hormone and hormone derivative is preferably selected from Flutamide, Fosfestrol, Tamoxifen and Relaxin. Further suitable hormones or hor-mone derivatives for use as payload according to the present invention are, for example, aminogluthemid, buserilin, cyproteronacetate, droloxifen, ethinylestradiol, flutamid, formesta, fosfestrol, gestonoroncaproate, goserilin, leupro-lein, lynestrenol, medrogeston, medroxyprogesteronacetate, megestrolactetate, octreotid, relaxin, tamoxifen, toremifin, triptorelin, anastrazole, exemestane, or letrozole.

As further understood herein suitable miRNAs and siR-NAs are, for example, those that are specific for CD40, CD80 and CD86, and also any agents that target clustered regularly interspaced short palindromic repeat (CRISPR) components for gene-editing purposes, or antigens that modulate the immune system, for example, insulin-associ-ated antigens, P31, whole gliadin, myelin oligodendrocyte glycoprotein (preferably amino acids 35-55), proteolipid protein 1 (preferably amino acids 139-151 and 178-191), Factor V (preferably amino acids 75-89, 1723-1737 and 2191-2210).

It is to be understood that radionuclides, are preferably not bound directly to the fibronectin binding peptide of the invention or the linker but are comprised in a complexing or chelator which can be conjugated as payload to the fibronec-tin binding peptide of the invention. Thus, as understood herein, a reference to radionuclide as payload is meant to be understood as a chelator charger with a radionuclide. Chela-tors that may be conjugated to the fibronectin binding peptide of the invention include, but are not limited to, 1,4,7,10-tetraazacyclododecane-1,4,7,10-tetraacetic acid (DOTA), diethylenetriaminepentaacetic (DTPA), desferri-oxamine (DFO) and triethylenetetramine (TETA), 1,4,8,11-tetraazabicyclo[6.6.2]hexadecane-4,11-diacetic acid (CB-TE2A); ethylenediaminetetraacetic acid (EDTA); ethylene glycolbis(2-aminoethyl)-N,N,N',N'-tetraacetic acid (EGTA); 1,4,8,11-tetraazacyclotetradecane-1,4,8,11-tet-raacetic acid (TETA); ethylenebis-(2-4 hydroxy-phenylgly-cine) (EHPG); 5-CI-EHPG; 5BrEHPG; 5-Me-EHPG; 5t-Bu-EHPG; 5-sec-Bu-EHPG; benzodiethylenetriamine pentaacetic acid (benzo-DTPA); dibenzo-DTPA; phenyl-DTPA, diphenyl-DTPA; benzyl-DTPA; dibenzyl-DTPA; bis-2(hydroxybenzyl)-ethylene-diaminediacetic acid (HBED) and derivatives thereof; Ac-DOTA; benzo-DOTA; dibenzo-DOTA; 1,4,7-triazacyclononane N,N',N'''-triacetic acid (NOTA); benzo-NOTA; 1,4,7-triazacyclononane N,N'-diacetic acid N''-glutaminic acid (NODAGA), benzo-TETA, benzo-DOTMA, where DOTMA is 1,4,7,10-tetraazacyclo-tetradecane-1,4,7,10-tetra(methyl tetraacetic acid), benzo-TETMA, where TETMA is 1,4,8,11-tetraazacyclotetrade-cane-1,4,8,11-(methyl tetraacetic acid); derivatives of 1,3-propylenediaminetetraacetic acid (PDTA); triethylenetetraaminehexaacetic acid (TTHA); derivatives of 1,5,10-N,N',N''-tris(2,3-dihydroxybenzoyl)-tricatecholate (LICAM); and 1,3,5-N,N',N''-tris(2,3-dihydroxybenzoyl) aminomethylbenzene (MECAM), or other metal chelators. In certain embodiments, the payload may comprise more than one chelator. Other preferred chelators can be selected from the group consisting of cyclic DPT A (diethylene triaminepentaacetic acid) anhydride, ethylenediaminetet-raacetic acid (EDTA), DOTA (1,4,7,10-tetraazacyclodode-cane-1,4,7,10-tetraacetic acid), and OTA (I,4,7-triazonane-I,4,7-triacetic acid).

As further understood herein, radionuclide is in certain embodiments preferably selected from are ⁶⁷Cu, ⁹⁰Y, ¹¹¹In, ¹³¹I, ¹⁶¹Tb, ¹⁶⁹Er, and ¹⁷⁷Lu. An especially preferred radio-nuclide for use in the present invention is ¹⁷⁷Lu or ¹³¹I.

Alternatively, the radionuclide can be selected from the group consisting of $^{90}$Y and $^{111}$In. Further suitable radionuclides include those emitting $\beta^+$ ($^{62}$Cu, $^{64}$Cu, $^{68}$Ga, $^{76}$Br, $^{82}$Rb, $^{124}$I, $^{44}$Sc, $^{43}$Sc, $^{89}$Sr or any other $\beta^+$ emitting isotope), $\beta$ (e.g. $^{90}$Y, $^{177}$Lu, $^{161}$Tb, $^{64}$Cu, $^{67}$Cu, $^{47}$Sc or any other B emitting isotope), a ($^{225}$Ac, $^{213}$Bi, $^{211}$At, $^{223/25}$Ra or any other a emitting isotope), or Auger electron emitter ($^{161}$Tb, $^{169}$Er, $^{111}$In or any other Auger electron emitting isotope), or any combination of therapeutic applicable radio-emissions.

Most preferably, the biologically active molecule is selected from the group consisting of Paclitaxel, Chlorambucil, Endostatin, Sunitinib, Interleukin-7, $^{177}$Lu, and $^{111}$In.

In a further embodiment of the present invention, the payload is an imaging agent. The imaging agent may be any imaging agent known in the art. The fibronectin binding peptide of the invention, when conjugated to an imaging agent, may be used in the visualization of cells and/or tissues in vitro and/or in vivo. When the fibronectin binding peptide is used for the visualization of a target cell or tissue in vitro, care has to be taken an imaging agent is selected that is functional under the imaging conditions. Similar criteria apply for imaging agents that are used for the visualization of target cells and/or tissues in vivo. However, for in vivo applications, additional care has to be taken that the imaging agent is biocompatible, e.g. has no toxic or otherwise detrimental effects on the subject that compound of the invention comprising the imaging agent is administered to.

The term "imaging agent" as used herein refers to any element, molecule, functional group, compound, fragments thereof or moiety that facilitates detection of an agent (e.g., the compound of the invention) to which it is conjugated. Examples of imaging agents include, but are not limited to: various ligands, radionuclides, fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductor nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available. It is to be understood that the imaging agent may be conjugated to the fibronectin binding peptide of the invention directly or indirectly via a linker, or that the imaging agent may be comprised in a molecule that is conjugated to the compound of the invention directly or indirectly via a linker. The skilled person would understand which imaging agents may be conjugated directly to the fibronectin binding peptide of the invention or a linker and which imaging agents need to be embedded in a molecule that can be conjugated to the compound of the invention or a linker. For example, if the imaging agent is a radionuclide, the radionuclide is preferably embedded in a molecule (e.g. chelated by a chelator being part of the said molecule) that can be conjugated to the fibronectin binding peptide of the invention or to the linker.

Preferably, the imaging agent comprises a radionuclide, a fluorescent dye, a chemiluminescent agent, a bioluminescent agent, a spectrally resolvable inorganic fluorescent semiconductor nanocrystal, a metal nanoparticle, a nanocluster, a paramagnetic metal ion, an enzyme, a colorimetric label, biotin, dioxigenin, a hapten or a protein. Preferably, the imaging agent comprises a radionuclide, fluorescent dye, a chemiluminescent agent, or a bioluminescent agent.

In another embodiment, the imaging agent is selected from the group consisting of radionuclide, MRI active compound, ultrasound contrast agent, fluorophore, marker for PET and SPECT, preferably selected from $^{44}$Sc, $^{64}$Cu, $^{67/68}$Ga $^{99m}$Tc, $^{111}$In, fluorophore in the far red/near-IR spectral region, and Gd-based and Fe-oxide particle based MRI contrast agent.

In again a further particular embodiment the present invention relates to the fibronectin binding peptide of the present invention, wherein the imaging agent is selected from $^{99m}$Tc, $^{111}$In, $^{44}$Sc and $^{64}$Cu.

In again a further particular embodiment the present invention relates to the fibronectin binding peptide of the present invention, wherein the payload comprises a radionuclide, preferably selected from $^{64}$Cu, $^{90}$Y, $^{111}$In, $^{131}$I, $^{161}$Tb, $^{169}$Er and $^{177}$Lu or preferably selected from $^{44}$Sc, $^{64}$Cu, $^{67/68}$Ga $^{99m}$Tc, and $^{111}$In.

In certain embodiments, the fibronectin-binding peptide of the invention may be conjugated to one or more contrast/imaging agents (e.g., fluorescent dyes, (chelated) radionuclides (SPECT, PET), MR-active agents, CT-agents).

In certain embodiments, a contrast/imaging agent may be conjugated to the fibronectin binding peptide of the invention for medical or biological imaging. The fibronectin binding peptides of the present invention may be useful in certain imaging techniques, which may include positron emission tomography (PET), single photon emission computed tomography (SPECT), computerized tomography (CT), magnetic resonance imaging (MRI), optical bioluminescence imaging, optical fluorescence imaging, and combinations thereof. In certain embodiments, the contrast/imaging agent may be any molecule, substance or compound known in the art for PET, SPECT, CT, MRI, and optical imaging. The contrast agent may be radionuclides, radiometals, positron emitters, beta emitters, gamma emitters, alpha emitters, paramagnetic metal ions, and suprapara-magnetic metal ions. The contrast agents include, but are not limited to, iodine, fluorine, Cu, Zr, Lu, At, Yt, Ga, In, Tc, Gd, Dy, Fe, Mn, Ba and $BaSO_4$.

In certain embodiments, the imaging agent may be a fluorescent reporter. In certain embodiments, the fluorescent reporter may be a near infrared or far red dye. In certain embodiments, the fluorescent reporter may be selected from the group consisting of a fluorophore, fluorochrome, dye, pigment, fluorescent transition metal, and fluorescent protein. In certain embodiments, the fluorescent reporter is selected from the group consisting of Cy5, Cy5.5, Cy2, FITC, TRITC, Cy7, FAM, Cy3, Cy3.5, Texas Red, ROX, HEX, JA133, AlexaFluor 488, AlexaFluor 546, AlexaFluor 633, AlexaFluor 555, AlexaFluor 647, DAPI, TMR, R6G, GFP, enhanced GFP, CFP, ECFP, YFP, Citrine, Venus, YPet, CyPet, AMCA, Spectrum Green, Spectrum Orange, Spectrum Aqua, Lissamine and Europium.

Exemplary imaging agents include, for example, the following: Cy5.5, Cy5, Cy7.5 and Cy7 (GE® Healthcare); AlexaFluor660, AlexaFluor680, AlexaFluor790, and AlexaFluor750 (Invitrogen); VivoTag™680, VivoTag™-S680, VivoTag™-S750 (VISEN Medical); Dy677, Dy682, Dy752 and Dy780 (Dyomics®); DyLight®547, and/or DyLight® 647 (Pierce); HiLyte Fluor™ 647, HiLyte Fluor™ 680, and HiLyte Fluor™ 750 (AnaSpec®); IRDye® 800CW, IRDye® 800RS, and IRDye® 700DX (Li-Cor®); ADS780WS, ADS830WS, and ADS832WS (American Dye Source); XenoLight CF™ 680, XenoLight CF™ 750, Xeno-Light CF™ 770, and XenoLight DiR (Caliper® Life Sciences); and Kodak® X-SIGHT® 650, Kodak®X-SIGHT 691, Kodak®X-SIGHT 751 (Carestream® Health).

Preferably the fibronectin binding peptide of the present invention relates to an embodiment, wherein the payload is [$^{111}$In]In-NODAGA moiety.

Further envisaged by the present invention are compounds, wherein two fibronectin binding peptide, preferably wherein each said fibronectin binding peptide is conjugated to a payload, are linked together or conjugated to each other in a way that preserves the possibility of binding of each of said fibronectin binding peptides to fibronectin. For example, each said fibronectin binding peptide may be conjugated to a payload through its C-terminus, and both fibronectin binding peptides may be linked to each other through their N-termini, or through a suitable linking moiety. Preferably, the payload is a radionuclide.

Pharmaceutical Compositions

In a further embodiment, the present invention relates to a pharmaceutical composition comprising the fibronectin binding peptide as described herein and a pharmaceutically acceptable carrier. As detailed herein, the fibronectin binding peptide of the invention, preferably including a payload-conjugate (i.e., a biologically active molecule or an imaging agent conjugated to the fibronectin binding peptide of the invention either directly or indirectly via a linker) may affect targeting of the payload to the a target cell or tissue. In certain embodiments, the payload-conjugate may also affect intracellular transport of the payload into a target cell. Accordingly, in preferred embodiments, the invention encompasses a pharmaceutical composition comprising a fibronectin-binding peptide of the invention, e.g., a payload-conjugate, and a pharmaceutically acceptable carrier or excipient.

Such a carrier or excipient includes, but is not limited to, saline, buffered saline, dextrose, water, glycerol, ethanol, and/or combinations thereof. The pharmaceutical compositions also may include additional therapeutic agents for the treatment of the given disease being treated. The formulation is made to suit the mode of administration. In general, methods of administering polypeptides are well known in the art and can be applied to administration of the conjugates of the invention.

Administration is by any of the routes normally used for introducing a fibronectin-binding peptide into ultimate contact with blood. Suitable methods of administering such fibronectin-binding peptide and their conjugates in the context of the present invention to a patient are available including oral and parenteral routes. Although more than one route can be used to administer a particular composition, a particular route can often provide a more immediate and more effective action or reaction than another route.

Preferably the payload-conjugates of the fibronectin-binding peptide of the invention are administered by parenteral modes of administration, in particular by intravenous, intraperitoneal, intramuscular, intradermal, subcutaneous intrathecal, intraocular, retrobulbar, intrapulmonary or intraarticular means. Such administration routes and appropriate formulations are generally known to those of skill in the art. Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilisers, thickening agents, stabilizers, and preservatives. Fibronectin-binding peptide and their conjugates can also be administered via liposomes.

The fibronectin-binding peptides and conjugates thereof of the invention, alone or in combination with other suitable components, can also be made into aerosol formulations (i.e., they can be "nebulised") to be administered via inhalation. Aerosol formulations can be placed into pressurized acceptable propellants, such as dichlorodifluoromethane, propane, nitrogen, and the like.

In a preferred embodiment, the pharmaceutical compositions of the invention are provided in lyophilized form to be reconstituted prior to administration. Buffers and solutions for the reconstitution of the pharmaceutical compositions may be provided along with the pharmaceutical formulation to produce aqueous compositions of the present invention for administration.

Pharmaceutically acceptable carriers are determined in part by the particular composition being administered, as well as by the particular method used to administer the composition. Accordingly, there are a wide variety of suitable formulations of pharmaceutical compositions of the present invention. Pharmaceutically acceptable carriers and excipients are well known in the art, and one or more conjugates of the invention can be formulated into pharmaceutical compositions by well-known methods (see, e.g., Remington: The Science and Practice of Pharmacy, 21st edition, A. R. Gennaro, Ed., Mack Publishing Company (2005); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)).

Pharmaceutical compositions comprising one or more fibronectin-binding peptides and/or payload-conjugates thereof of the invention are optionally tested in one or more appropriate in vitro and/or in vivo animal models of disease, to confirm efficacy, tissue metabolism, and to estimate dosages, according to methods well known in the art. Thus, it is understood that the suitable dose of a composition according to the present invention will depend upon the age, health and weight of the recipient, kind of concurrent treatment, if any, frequency of treatment, and the nature of the effect desired. However, the dosage is tailored to the individual subject, as is determinable by one of skill in the art, without undue experimentation. The total dose of therapeutic agent may be administered in multiple doses or in a single dose. In certain embodiments, the compositions are administered alone, in other embodiments the compositions are administered in conjunction with other therapeutics directed to the disease or directed to other symptoms thereof.

The fibronectin binding peptides in the present invention may be administered alone or in combination with adjuvants that enhance stability, facilitate administration of pharmaceutical compositions containing them, provide increased dissolution or dispersion, increase inhibitory activity, provide adjunct therapy, and the like, including other active ingredients. Advantageously such combination therapies utilize lower dosages of the conventional therapeutics, thus avoiding possible toxicity and adverse side effects incurred when those agents are used as monotherapies. The above described fibronectin binding peptides may be physically combined with the conventional therapeutics or other adjuvants into a single pharmaceutical composition.

The dose administered to a patient, in the context of the present invention, is sufficient to affect a beneficial therapeutic response in the patient over time, or, e.g., to inhibit infection by a pathogen, to reduce or prevent the symptoms of a disease state, or other appropriate activity, depending on the application. The dose is determined by the efficacy of a particular composition/formulation, and the activity, stability or serum half-life of the BAM polypeptide conjugate employed and the condition of the patient, as well as the body weight or surface area of the patient to be treated. The size of the dose is also determined by the existence, nature, and extent of any adverse side-effects that accompany the administration of a particular composition/formulation, or the like in a particular patient. In some embodiments, dosage levels range from about 0.5 μg-100 mg/dose for a 70 kg patient. Although one dose per day may be sufficient, up to 5 doses per day may be given. For oral doses, up to 2000 mg/day may be required. For radionuclide therapy a dose every 4 to 8 week for 2 to 8 times may be applicable. As the person skilled in the art will appreciate, lower or higher doses may be required depending on particular factors. For instance, specific doses and treatment regimens will depend on factors such as the patient's general health profile, the severity and course of the patient's disorder or disposition thereto, and the judgment of the treating physician. For example, the fibronectin binding peptides of the present invention can be administered the same way as other peptide-based medicaments.

The fibronectin binding peptides in the present invention may be formulated into capsules the same way other peptide-based medicaments are formulated. Each capsule may contain 100 to 500, preferably 150 to 300, more preferably 200 to 250 mg of a compound of the invention. For example, non-medicinal ingredients in capsules for the compounds of the present invention are—capsule shell: D&C yellow No. 10, FD&C blue No. 1, FD&C red No. 3, FD&C yellow No. 6, gelatin and titanium dioxide. Bottles of 100. (see also Martindale: the complete drug reference, 34 Edition, 2005, Pharmaceutical Press, p 612.).

Therapeutic Application

In one embodiment, the present invention relates to the fibronectin binding peptide of the present invention as described hereinabove or the pharmaceutical composition of the present invention as described hereinabove for use in therapy. Therapy is herein preferably understood as treatment and/or prevention, more preferably as treatment.

In a further embodiment, the present invention relates to the fibronectin binding peptide of the present invention as described hereinabove, or the pharmaceutical composition of the present invention for use in the treatment or prevention of a disease associated with pathologic fibronectin accumulation. The term "pathological fibronectin accumulation" as used herein, refers to any disease or condition in which the amount of fibronectin deposited at a given site is higher than in a healthy state. For example, pathological fibronectin accumulation is found regularly in fibrosis or cancer.

As used herein, the term "fibrosis" can refer to any disease characterized by fibrosis, including but not limited to systemic sclerosis, multifocal fibrosclerosis, sclerodermatous graft-vs-host-disease, nephrogenic systemic fibrosis, organ specific fibrosis, mediastinal fibrosis, myelofibrosis, retroperitoneal fibrosis, progressive massive fibrosis, Crohn's Disease, Keloid, arthrofibrosis, Peyronie's Disease, Dupuytren's Contracture, adhesive capsulitis, and the like. Illustrative organ specific fibrosis include, but are not limited to, pulmonary fibrosis, pulmonary hypertension, cystic fibrosis, asthma, chronic obstructive pulmonary disease, liver fibrosis, kidney fibrosis, fibrosis of the pancreas, non-alcoholic steatohepatitis (NASH), lymph node fibrosis, corneal fibrosis, fibrous cartilage, endometriosis, and the like. Many fibrosis diseases, disorders or conditions have disordered and/or exaggerated deposition of extracellular matrix in affected tissues. Fibrosis may be associated with inflammation, occur as a symptom of underlying disease, and/or caused by surgical procedure or injuries with limited wound healing capacities.

A "cancer" or "tumor" as used herein refers to an uncontrolled growth of cells which interferes with the normal functioning of the bodily organs and systems. Examples of cancer include, but are not limited to B-cell lymphomas (Hodgkin's lymphomas and/or non-Hodgkin's lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma and other skin cancers, head and neck cancer (preferably head and neck squamous cell carcinoma), brain cancer, and prostate cancer, including but not limited to androgen-dependent prostate cancer and androgen-independent prostate cancer.

Preferably, the disease associated with pathogenic fibronectin accumulation is a disease associated with abnormal accumulation of soluble plasma fibronectin and/or insoluble ECM fibronectin. Thus, the present invention relates to the fibronectin binding peptide of the present invention as described hereinabove or the pharmaceutical composition of the present invention as described hereinabove for use in the treatment and/or prevention of a disease associated with abnormal accumulation of soluble plasma fibronectin and/or insoluble ECM fibronectin Further preferably, the disease associated with pathologic fibronectin accumulation is selected from the group consisting of fibrosis, cancer, lymphedema, immune disease, autoimmune disease, and atherosclerosis. Thus, the present invention relates to the fibronectin binding peptide of the present invention as described hereinabove or the pharmaceutical composition of the present invention as described hereinabove for use in the treatment and/or prevention of a disease selected from fibrosis, cancer, lymphedema, immune disease, autoimmune disease, and atherosclerosis.

As understood herein the autoimmune diseases is preferably selected from systemic sclerosis, diabetes type 1, Graves' disease, multiple sclerosis and rheumatoid arthritis. Thus, the present invention relates to the fibronectin binding peptide of the present invention as described hereinabove or the pharmaceutical composition of the present invention as described hereinabove for use in the treatment and/or prevention of a disease selected from systemic sclerosis, diabetes type 1, Graves' disease, multiple sclerosis and rheumatoid arthritis.

As further understood herein, preferably the fibrosis is selected from pulmonary fibrosis, liver fibrosis, and kidney fibrosis. Thus, the present invention relates to the fibronectin binding peptide of the present invention as described hereinabove or the pharmaceutical composition of the present invention as described hereinabove for use in the treatment and/or prevention of a disease selected from pulmonary fibrosis, liver fibrosis, and kidney fibrosis.

As further understood herein, the cancer is preferably selected from breast cancer, head and neck squamous cell carcinoma, prostate cancer, renal cancer, pancreatic cancer and lung cancer. Thus, the present invention relates to the fibronectin binding peptide of the present invention as described hereinabove or the pharmaceutical composition of the present invention as described hereinabove for use in the treatment and/or prevention of a disease selected from breast cancer, head and neck squamous cell carcinoma, prostate cancer, renal cancer, pancreatic cancer and lung cancer.

Preferably, the lung cancer is a non-small lung cell cancer. Thus, the present invention relates to the fibronectin binding peptide of the present invention as described hereinabove or the pharmaceutical composition of the present invention as described hereinabove for use in the treatment and/or prevention of non-small cell lung cell cancer.

In one embodiment, the disease associated with pathologic fibronectin accumulation is endometriosis.

The present invention further relates to use of the fibronectin binding peptide of the present invention as described hereinabove, or the pharmaceutical composition of the present invention for the manufacture of a medicament for use in the treatment or prevention of a disease associated with pathologic fibronectin accumulation. The disease associated with pathologic fibronectin accumulation is as described hereinabove.

Thus accordingly, the present invention further relates to use of the fibronectin binding peptide of the present invention as described hereinabove, or the pharmaceutical composition of the present invention for the manufacture of a medicament for use in the treatment or prevention of a disease associated with abnormal accumulation of soluble plasma fibronectin and/or insoluble ECM fibronectin.

Further accordingly, the present invention further relates to use of the fibronectin binding peptide of the present invention as described hereinabove, or the pharmaceutical composition of the present invention for the manufacture of a medicament for use in the treatment or prevention of a disease selected from fibrosis, cancer, lymphedema, immune disease, autoimmune disease, and atherosclerosis.

Further accordingly, the present invention further relates to use of the fibronectin binding peptide of the present invention as described hereinabove, or the pharmaceutical composition of the present invention for the manufacture of a medicament for use in the treatment or prevention of a disease selected from systemic sclerosis, diabetes type 1, Graves' disease, multiple sclerosis and rheumatoid arthritis.

Further accordingly, the present invention further relates to use of the fibronectin binding peptide of the present invention as described hereinabove, or the pharmaceutical composition of the present invention for the manufacture of a medicament for use in the treatment or prevention of a disease selected from pulmonary fibrosis, liver fibrosis, and kidney fibrosis.

Further accordingly, the present invention further relates to use of the fibronectin binding peptide of the present invention as described hereinabove, or the pharmaceutical composition of the present invention for the manufacture of a medicament for use in the treatment or prevention of a disease selected from breast cancer, head and neck squamous cell carcinoma, prostate cancer, renal cancer, pancreatic cancer and lung cancer.

Further accordingly, the present invention further relates to use of the fibronectin binding peptide of the present invention as described hereinabove, or the pharmaceutical composition of the present invention for the manufacture of a medicament for use in the treatment or prevention of non-small cell lung cell cancer.

Further accordingly, the present invention further relates to use of the fibronectin binding peptide of the present invention as described hereinabove, or the pharmaceutical composition of the present invention for the manufacture of a medicament for use in the treatment or prevention of endometriosis.

In a further embodiment, the present invention relates to a method of treatment or prevention (preferably to a method of treatment) of a disease associated with pathologic fibronectin accumulation. The said method comprises the step of administering the therapeutically effective amount of the fibronectin binding peptide of the present invention or the pharmaceutical composition of the present invention to the subject in need thereof. The subject herein is preferably defined as a human subject, preferably suffering from a disease associated with pathologic fibronectin accumulation. The disease associated with pathologic fibronectin accumulation is as defined hereinabove.

Thus accordingly, the present invention further relates to a method of treatment or prevention (preferably to a method of treatment) of a disease associated with abnormal accumulation of soluble plasma fibronectin and/or insoluble ECM fibronectin. The said method comprises the step of administering the therapeutically effective amount of the fibronectin binding peptide of the present invention or the pharmaceutical composition of the present invention to the subject in need thereof.

Further accordingly, the present invention further relates to a method of treatment or prevention (preferably to a method of treatment) of a disease selected from fibrosis, cancer, lymphedema, immune disease, autoimmune disease, and atherosclerosis. The said method comprises the step of administering the therapeutically effective amount of the fibronectin binding peptide of the present invention or the pharmaceutical composition of the present invention to the subject in need thereof.

Further accordingly, the present invention further relates to a method of treatment or prevention (preferably to a method of treatment) of a disease selected from systemic sclerosis, diabetes type 1, Graves' disease, multiple sclerosis and rheumatoid arthritis. The said method comprises the step of administering the therapeutically effective amount of the fibronectin binding peptide of the present invention or the pharmaceutical composition of the present invention to the subject in need thereof.

Further accordingly, the present invention further relates to a method of treatment or prevention (preferably to a method of treatment) of a disease selected from pulmonary fibrosis, liver fibrosis, and kidney fibrosis. The said method comprises the step of administering the therapeutically effective amount of the fibronectin binding peptide of the present invention or the pharmaceutical composition of the present invention to the subject in need thereof.

Further accordingly the present invention further relates to a method of treatment or prevention (preferably to a method of treatment) of a disease selected from breast cancer, head and neck squamous cell carcinoma, prostate cancer, renal cancer, pancreatic cancer and lung cancer. The said method comprises the step of administering the therapeutically effective amount of the fibronectin binding peptide of the present invention or the pharmaceutical composition of the present invention to the subject in need thereof.

Further accordingly, the present invention further relates to a method of treatment or prevention (preferably to a method of treatment) of non-small cell lung cell cancer. The said method comprises the step of administering the therapeutically effective amount of the fibronectin binding peptide of the present invention or the pharmaceutical composition of the present invention to the subject in need thereof.

Further accordingly, the present invention further relates to a method of treatment or prevention (preferably to a method of treatment) of endometriosis. The said method comprises the step of administering the therapeutically effective amount of the fibronectin binding peptide of the present invention or the pharmaceutical composition of the present invention to the subject in need thereof.

Particularly useful fibronectin binding peptides of the present invention are those bearing a biologically active molecule as a payload, as described hereinabove.

Diagnostic Use

In a further embodiment, the present invention relates to the fibronectin binding peptide of the present invention or the pharmaceutical composition of the present invention for use in diagnosis. Preferably, the present invention relates to the fibronectin binding peptide of the present invention or the pharmaceutical composition of the present invention for use in diagnosis of a disease associated with pathologic fibronectin accumulation. The disease associated with pathologic fibronectin accumulation is as described hereinabove.

The fibronectin binding peptide of the present invention or the pharmaceutical composition of the present invention are useful in diagnosis of a disease selected from the group consisting of fibrosis, cancer, lymphedema, immune disease, autoimmune disease, and atherosclerosis. Thus, the present invention relates to the fibronectin binding peptide of the present invention or the pharmaceutical composition of the present invention for use in diagnosis of a disease selected from the group consisting of fibrosis, cancer, lymphedema, immune disease, autoimmune disease, and atherosclerosis.

Further accordingly, the present invention relates to the fibronectin binding peptide of the present invention or the pharmaceutical composition of the present invention for use in diagnosis of autoimmune diseases, preferably selected from systemic sclerosis, diabetes type 1, Graves' disease, multiple sclerosis and rheumatoid arthritis.

Further accordingly, the present invention relates to the fibronectin binding peptide of the present invention or the pharmaceutical composition of the present invention for use in diagnosis of fibrosis, preferably selected from pulmonary fibrosis, liver fibrosis, and kidney fibrosis.

Further accordingly, the present invention relates to the fibronectin binding peptide of the present invention or the pharmaceutical composition of the present invention for use in diagnosis of cancer, preferably selected from breast cancer, head and neck squamous cell carcinoma, prostate cancer, renal cancer, pancreatic cancer and lung cancer.

Further accordingly, the present invention relates to the fibronectin binding peptide of the present invention or the pharmaceutical composition of the present invention for use in in diagnosis of non-small lung cell cancer.

Further accordingly, the present invention relates to the fibronectin binding peptide of the present invention or the pharmaceutical composition of the present invention for use in in diagnosis of endometriosis.

Accordingly, the present invention relates to a method of diagnosing a disease associated with pathologic fibronectin accumulation in a subject, the method comprising the step of administering the fibronectin binding peptide of the present invention to a subject and the step of detecting the pathologic fibronectin accumulation in said subject. It is to be understood that the fibronectin binding peptide useful in a method of diagnosing is preferably conjugated to an imaging agent or a radionuclide. It is further to be understood that the pathologic fibronectin accumulation is detected by detecting the accumulation of the fibronectin binding peptide of the present invention at the site of said pathologic fibronectin accumulation.

Particularly useful fibronectin binding peptides of the present invention are those bearing an imaging agent as a payload, as described hereinabove.

EXAMPLES

The following examples are merely illustrative of the present invention and should not be construed to limit the scope of the invention which is defined by the appended claims.

Preparative Example 1—Preparation of NODAGA- or Cy5-Labelled Fibronectin Binding Peptides NODAGA- and/or Cyanine5 (Cy5) conjugated fibronectin-binding peptides (of FnBPA5.1 sequence according to SEQ ID NO: 12 or of FnBPA5 sequence according to SEQ ID NO: 13) were synthesized to obtain HPLC purity greater than 95%. The peptide-conjugates were synthetized via introduction of the desired moiety (e.g. NODAGA or Cy5) at the N-terminus of the fibronectin-binding peptide via amide bond formation or maleimide-thiol conjugation. A short spacer of three glycines (and an additional cysteine residue in the case of conjugates obtained via maleimide-thiol chemistry) between the last N-terminal amino-acid of the fibronectin-binding peptide and the payload (herein NODAGA, Cy5) was added, resulting in the following structure:

payload-GGG-fibronectin-binding peptide or payload-CGGG-fibronectin-binding peptide The peptide-conjugates were obtained as lyophilized powders in HPLC purity greater than 95%. Linear peptide sequences were synthesized via automatized solid-phase peptide synthesis employing standard Fmoc/tBu protocols, following which a final conjugation step via maleimide-thiol conjugation at the N-terminus of the fibronectin-binding sequence provided the final NODAGA or Cy5-conjugates. A short spacer of three glycines and an additional cysteine residue between the last N-terminal amino-acid of the fibronectin-binding sequence and the functionalization (chelator, dye) was introduced.

NODAGA-FnBPA5.1 (sequence: Ac-C(Mal-NODAGA)-GGG-QVTTGSNLVEFTEESLGIVTGAVSDHTTVEDT) (SEQ ID NO: 16) was obtained from Bachem (Bubendorf, Switzerland) upon conjugation of the N-terminal Cys-activated sequence with Maleimide-NODAGA (Chematech, Dijion, France).

Cy5-FnBPA5.1 (sequence: C(Mal-Cy5)-GGG-QVTTG-SNLVEFTEESLGIVTGAVSDHTTVEDT) (SEQ ID NO: 17) was obtained upon conjugation of the N-terminal Cys-activated sequence (Cys-FnBPA5.1, PSL GmbH, Heidelberg, Germany) with Cy5-Maleimide (Lumiprobe, Hannover, Germany). Cys-FnBPA5.1 was dissolved in PBS (50 mM, pH 5.5) to a conc. of 30 mM. Following Cy5-Maleimide addition (1 equiv.), the solution was stirred up to 2 h. Upon dilution (×10), the mixture was directly purified by means of RP-HPLC (Merck-Hitachi LaChrom HPLC) on a Jupiter Proteo 90 Å, 4 μm, 250×10 mm, Phenomenex (Aschaffenburg, Germany) RP C18 semi-preparative column. MeCN+0.1% TFA (A) and H2O+0.1% TFA (B) were employed as mobile phases and a gradient of 30 to 90% A in B over 15 minutes was employed. Upon lyophilization, Cy5-FnBPA5.1 was obtained as a blue powder in >95% purity. MALDI-FTICR-MS: m/z calculated [M+H]+ for Cy5-FnBPA5.1 4215.0114; found: 4215.0114.

To prepare [$^{111}$In]In-NODAGA-FnBPA5.1, NODAGA-FnBPA5.1 was dissolved in 10% DMF TraceSELECT® Water (Sigma-Aldrich, Buchs, Switzerland) at 1 mg/mL, and further diluted with TraceSELECT® Water to a final concentration of 0.1 mM. The conjugate was labeled with

[¹¹¹In]InCl₃ (Mallinckrodt, Wollerau, Switzerland) in metal-free ammonium acetate (0.5 M, pH 5.5) at a molar activity of 6 MBq/nmol, followed by a 15 min incubation step at 50° C. An Eppendorf Thermomixer comfort (Eppendorf, Hamburg, Germany) was used for heating and simultaneous shaking of the labelling mixture. Upon labelling, an aliquot of the reaction mixture was subjected to quality control by means of RP-γHPLC. RP-γHPLC of ¹¹¹In-labelled peptide was performed on an Agilent 1200 Series Gradient HPLC (Santa Clara, USA) equipped with a Gabi Star gamma detector (Raytest, Straubenhardt, Germany). MeCN+0.1% TFA (A) and H2O+0.1% TFA (B) were employed as mobile phases. Quality control of radio-labeling reactions was conducted on a ReproSil Pur, 120 Å, 3 μm, 100×4.6 mm (Dr. Maisch GmbH, Germany) RP C18 analytical column, with a gradient ranging from 10 to 80% A in B over 10 min, at a flow rate of 1 mL per min.

Example 1—Affinity Determination of Cy5-Labeled FnBPA5.1 Towards Fib1 Using Fluorescence Polarization For the affinity measurement experiment, Cy5-FnBPA5.1 (according to SEQ DI NO: 12) and Cy5-FnBPA5 (according to SEQ DI NO: 13) (48 nM) were mixed with different concentrations of Fib 1—N-terminal 30 kDa fragment of fibronectin according to SEQ ID NO: 14 (0 nM-4.5 μM) in PBS pH 7.4. Samples were incubated for 1 h (37° C., 70 rpm) and fluorescence polarization was measured in triplicates using the Pherastar FSX plate reader (BMG Labtech; Optic module: FP 590-50 675-50 675-50). Background fluorescence was subtracted and fluorescence polarization was converted to anisotropy and fitted using the binding equation described by Pallicer et al. (Pallicer, J. M., and Kramer, S. D. (2012) Evaluation of fluorescence anisotropy to assess drug-lipid membrane partitioning, J Pharm Biomed Anal 71, 219-227) to derive the dissociation constant $K_D$. The results are shown in FIG. 1.

Fib1, the 30 kDa N-terminal fragment of fibronectin containing the N-terminal FnI1-5 modules, was expressed in human embryonic kidney cells (HEK-293). For this, the cDNA of Fib1 containing a 6-His tag at the C-terminal end for affinity purification via Ni-NTA agarose (Qiagen, Basel, Switzerland) was cloned into the HindIII/BamHI site of the mammalian expression vector pcDNA3.1+ (Invitrogen, Basel, Switzerland). Proper cDNA insertion into the vector was confirmed by DNA sequencing (Microsynth, Balgach, Switzerland). HEK-293 cells were transfected using the calcium phosphate method. After Geneticin selection, the most efficient cell clone was used for production and Fib1 was purified from cell culture supernatants as previously described (Grunberg, J., Knogler, K., Waibel, R., and Novak-Hofer, I. (2003). High-yield production of recombinant antibody fragments in HEK-293 cells using sodium butyrate, Biotechniques 34, 968-972). Finally, Fib1 was dialyzed against PBS pH 7.4.

Example 2—Fibronectin Fiber Stretch Assay

Figure 2:
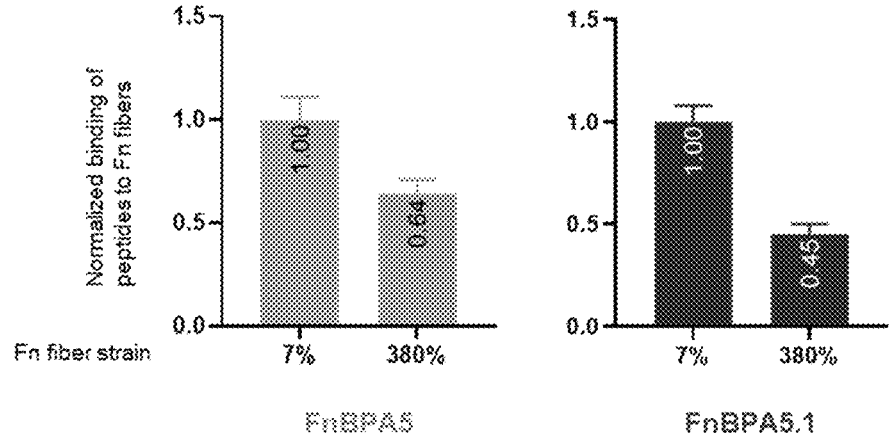
FIG. 2: Intensity ratio of Cy5-labelled peptides to Alexa488-labelled Fibronectin relaxed (7% strain) or stretched (380% strain) fibers. Normalized values: the mean of the intensity ratio of each peptide to relaxed Fibronectin fibers was set to 1 and the remaining value was scaled accordingly. Data from 10 to 15 fibers with error bars being standard deviations. P-values were obtained from unpaired two-tailed student's t-tests (Graph PadPrism).

Fibronectin was extracted from human blood plasma (Zürcher Blutspendedienst SRK, Switzerland) using gelatin sepharose chromatography. Fibronectin fibers were manually pulled from a concentrated droplet of fibronectin in PBS (95% unlabeled and 5% A488-labeled protein) using a sharp pipette tip and deposited onto a flexible silicone sheet (SMI, USA), rinsed and rehydrated in PBS. Thereafter, fibers were either relaxed (about 7% strain) or stretched (about 380% strain) as defined by Little et al. (Little, W. C., Smith, M. L., Ebneter, U. & Vogel, V. Assay to mechanically tune and optically probe fibrillar fibronectin conformations from fully relaxed to breakage. Matrix Biol. 27, 451-461 (2008)) After a blocking step with BSA (Sigma-Aldrich, Buchs, Switzerland) to avoid unspecific attachment of binding ligands to fibers or to the silicone sheet, the fibers were incubated with Cy5-labelled FnBPA5 or 5.1 (150 nM) for 1 h and imaged after a washing step by means of confocal microscopy. The results are shown in FIG. 2.

Example 3—Plasma Stability Studies

Figure 3:
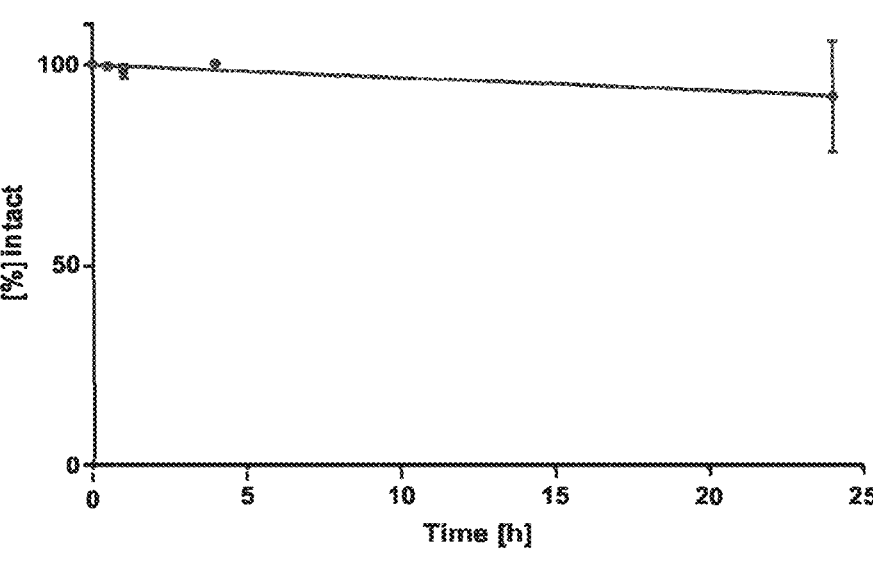
FIG. 3: Degradation kinetics of [$^{111}$In]In-FnBPA5.1 upon incubation in human blood plasma up to 24 h at 37° C. Data points show the mean±SD (n=3). Data was fitted by non-linear fit (GraphPad Prism).

Plasma stability of FnBPA5.1 was assessed by incubating 7.5 MBq of 111In[In]-NODAGA FnBPA5.1 in human blood plasma (Kantonsspital Aarau, Switzerland) at 37° C. under gentle agitation. At different time points (0, 0.5, 1, 4 and 24 h) aliquots were drawn and proteins were precipitated by the addition of an equal volume of MeCN. Upon centrifugation (14000 rpm, 10 min), the supernatant was filtered through a Mini-UniPrep Filter into a MiniPrep Whatman tube (Whatman Inc., NJ, USA) and analyzed by means of RP-γHPLC. Data are represented as percentages of recovered test compound at the individual time-points normalized to the reference sample at time 0 min. The results are shown in FIG. 3.

Example 4—Biodistribution in PC-3 Xenografts

Figure 4:
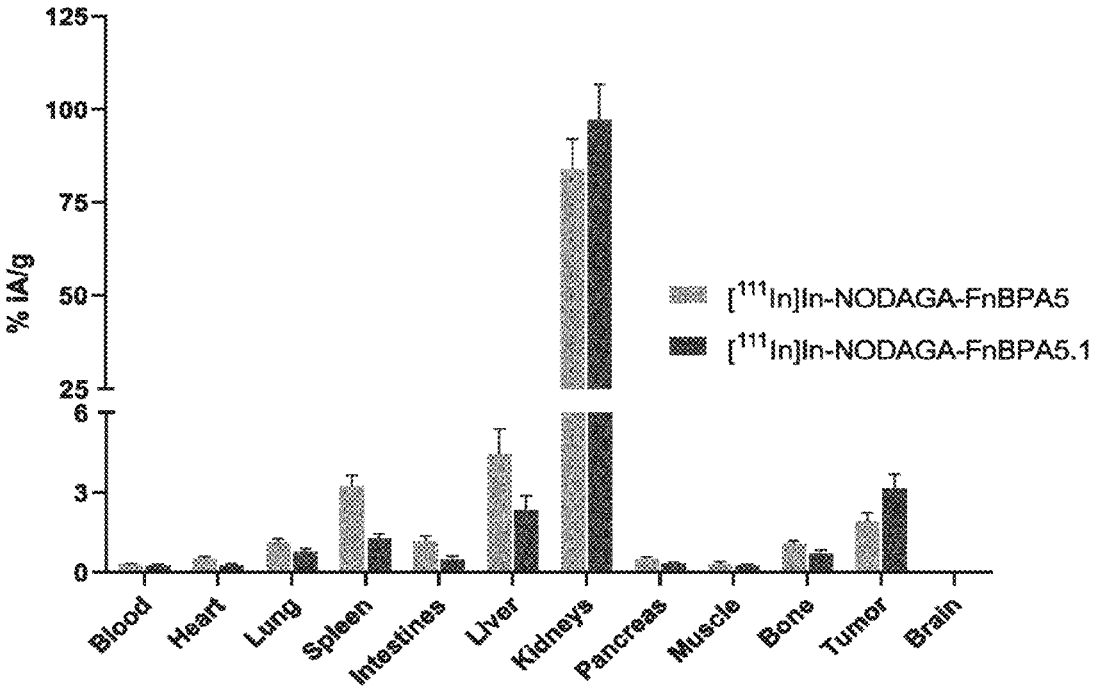
FIG. 4: Biodistribution of $^{111}$In-labeled NODAGA-FnBPA5 and its engineered version NODAGA-FnBPA5.1 in PC-3 tumor-bearing CD1 nu/nu mice 24 hours after injection. Results are shown as averages of % injected activity per gram±SD (n=4).

Animal studies were carried out according to the Swiss Animal Protection Law under the license AG75700. For tumor implantation, $5×10^6$ PC-3 cells in 100 μL PBS were injected subcutaneously into both shoulders of female CD1 nu/nu mice (Charles River, Germany) under isoflurane/oxygen anesthesia. Tumor growth was inspected regularly and tumors were measured using a caliper. Five weeks after tumor implantation, mice were injected via the tail vein with approximately 100-150 kBq of the corresponding ¹¹¹In-labelled radiotracers, previously diluted with PBS to a concentration of 1-1.5 MBq/mL. At 24 h p.i., mice were euthanized using $CO_2$. The organs of interest were harvested, weighed and counted by means of gamma counter together with three standards containing 100 μL of the injection solution. The percentage of injected activity per gram (% IA/g) was calculated based on the average of the standards set at 100%. The results are shown in FIG. 4.

Example 5—Biodistribution in a Orthotopic and Syngeneic Breast Tumor Model

Figure 5:
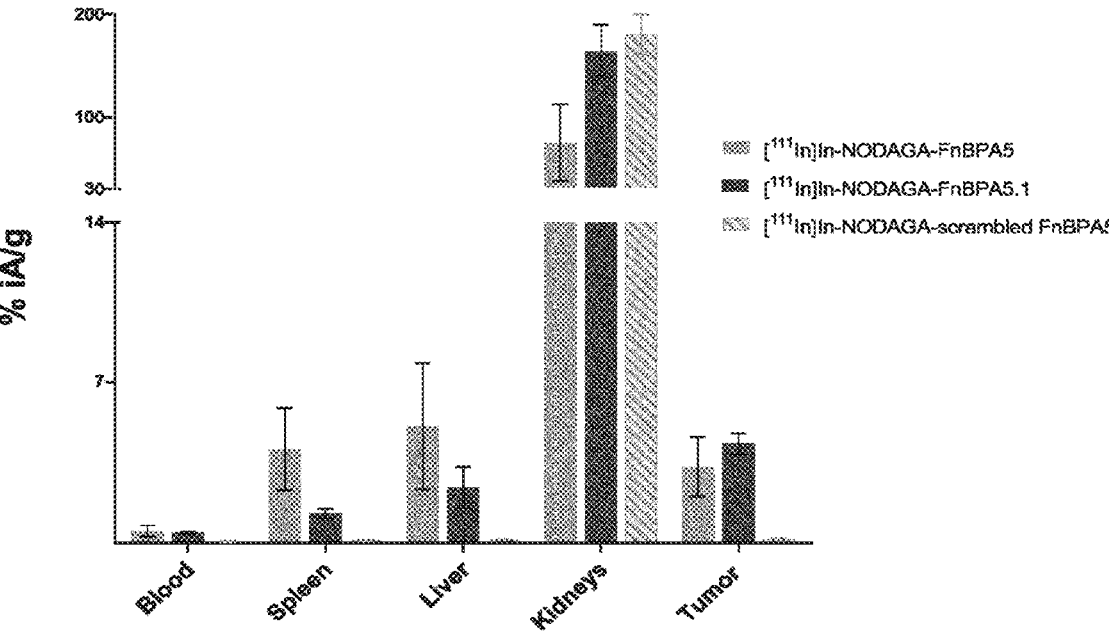
FIG. 5: Biodistribution of $^{111}$In-labeled NODAGA-FnBPA5 and its engineered version NODAGA-FnBPA5.1 in 67NR tumor-bearing mice 24 hours after injection. Results are shown as averages of % injected activity per gram±SD (n=4).

Animal studies were carried out according to the Swiss Animal Protection Law under the license AG75700. For tumor implantation, 40'000 67NR cells in 50 μL PBS were injected subcutaneously into the mammary fat pad at the 4ᵗʰ nipple of female Balb/c mice (Charles River, Germany) under isoflurane/oxygen anesthesia. Tumor growth was inspected regularly and tumors were measured using a caliper. Two weeks after tumor implantation, mice were injected via the tail vein with approximately 100-150 kBq of the corresponding ¹¹¹In-labelled radiotracers, previously diluted with PBS to a concentration of 1-1.5 MBq/mL. At 24 h p.i., mice were euthanized using $CO_2$. The organs of interest were harvested, weighed and counted by means of gamma counter together with three standards containing 100 μL of the injection solution. The percentage of injected activity per gram (% IA/g) was calculated based on the average of the standards set at 100%. The results are shown in FIG. 5.

Figure 6:
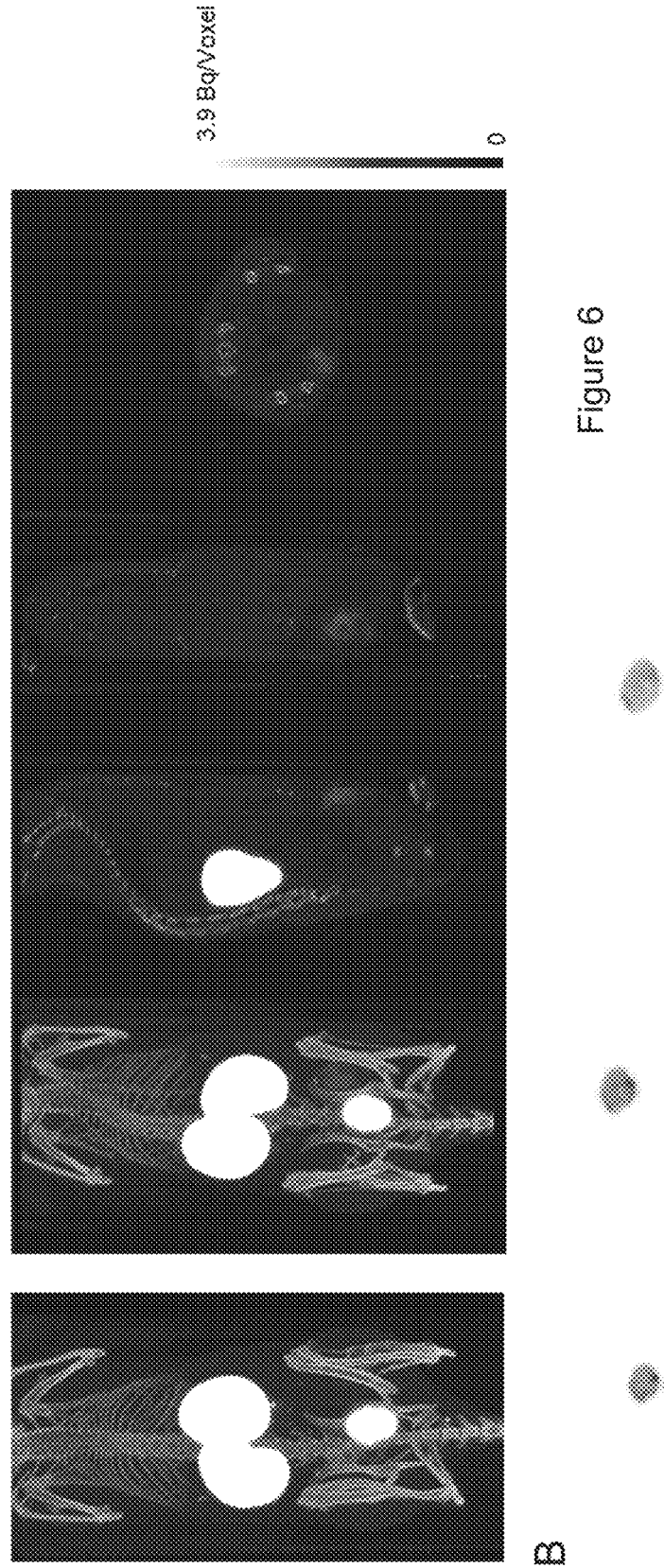
FIG. 6: SPECT images (A) and autoradiographs (B) 24 h after injection of [$^{111}$In]In-NODAGA FnBPA5.1 in a 67NR orthotopic and syngeneic breast tumor model.

Example 6—Orthotopic and Syngeneic Breast Tumor Model—SPECT/CT Imaging Studies Female Balb/c mice with a 67NR breast tumor were injected into the tail vein with 10-15 MBq of $^{111}$In-labelled NODAGA-FnBPA5.1, previously diluted with PBS to a concentration of 10-15 MBq/mL. At 24 h p.i., mice were put under isoflurane/oxygen anesthesia and subjected to a SPECT/CT scan with a NanoSPECT/CT camera (Mediso Medical Imaging Systems, Budapest, Hungary). Data was reconstructed with HiSPECT software (version 1.4.3049, Scivis GmbH, Gdttingen, Germany) and analyzed using VivoQuant (version 3.5, inviCRO Imaging Services and Software, Boston USA). SPECT images were processed after application of a post-reconstruction filter. Scale of activity was set to 0-3.9 Bq/voxel. The results are shown in FIG. 6A.

Example 7—Orthotopic and Syngeneic Breast Tumor Model—Autoradiography

After $CO_2$ euthanasia of SPECT/CT mice of Example 6, they were instantly perfused with 10 mL Ringer acetate supplemented with 50'000 units of Heparin through the right heart ventricle. Thereafter, 5 mL of OCT/PBS (50:50) were infused and tumors were excised and placed in OCT on dry ice. After full freezing, 10 µm cryosections were cut, dried for 30 min and exposed to a high resolution phosphor screen for 16 h. The screen was analyzed using a phosphor imager (Cyclone Plus, Perkin Elmer). The results are shown in FIG. 6B.

Example 8—Experimental Lung Disease Model of Fibrosis Induced Through Bleomycin-SPECT/CT Imaging Studies Female C57BL/6 mice were instilled with 2 U/kg body-weight Bleomycin (Bleomycin Baxter). For this mice were anesthetized by intraperitoneal injection of a mix of ketamine (80 mg/kg bodyweight) and xylazine (10 mg/kg). Mice were left in a chamber containing 100% oxygen for 5-10 min, before intra-tracheal application of Bleomycin.

Figure 7:
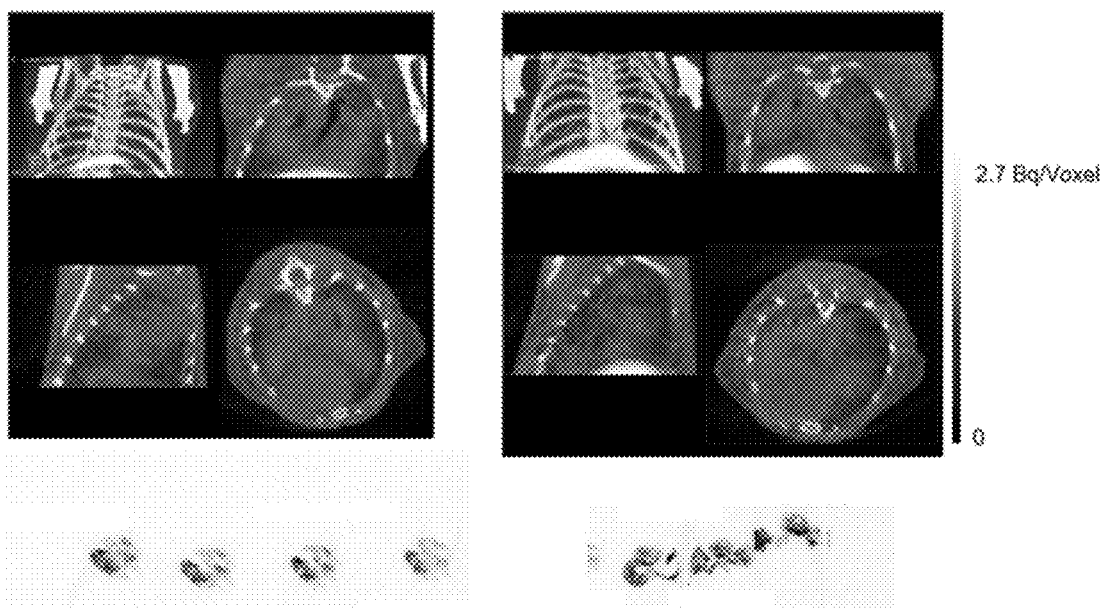
FIG. 7. SPECT images (top) and autoradiographs (bottom) of mice lungs 14 days after intra-tracheal instillation with Bleomycin and 24 h after injection of [$^{111}$In]In-NODAGA FnBPA5.1.

Two weeks after Bleomycin instillation, mice were injected into the tail vein with 10-15 MBq of [$^{111}$In]In-NODAGA FnBPA5.1, previously diluted with PBS to a concentration of 10-15 MBq/mL. At 24 h p.i., mice were put under isoflurane/oxygen anesthesia and subjected to a SPECT/CT scan with a NanoSPECT/CT camera (Mediso Medical Imaging Systems, Budapest, Hungary). Data was reconstructed with HiSPECT software (version 1.4.3049, Scivis GmbH, Gdttingen, Germany) and analyzed using VivoQuant (version 3.5, inviCRO Imaging Services and Software, Boston USA). SPECT images were processed after application of a post-reconstruction filter. Scale of activity was set to 0-2.6 Bq/voxel. The results are shown in FIG. 7.

Example 9—Experimental Lung Disease Model of Fibrosis Induced Through Bleomycin-Autoradiography After $CO_2$ euthanasia of SPECT/CT mice of Example 8, they were instantly perfused with 10 mL Ringer acetate supplemented with 50'000 units of Heparin through the right heart ventricle. Thereafter, 5 mL of OCT/PBS (50:50) were infused and tumors were excised and placed in OCT on dry ice. After full freezing, 10 µm cryosections were cut, dried for 30 min and exposed to a high-resolution phosphor screen for 16 h. The screen was analyzed using a phosphor imager (Cyclone Plus, Perkin Elmer). The results are shown in FIG. 7.

Example 10—PK Study: Protocol and Results

In this in vivo study, the test compound FNBPA5.1-MMAE conjugate (PDC) is evaluated in a PK study in non-tumor-bearing female BALB/c nude mice.

Test Animals:

Species: *Mus musculus*

Strain: BALB/c nude (CAnN.Cg-Foxn1nu)

Sex: Female

Source: Charles River GmbH

Sandhofer Weg 7

97633 Sulzfeld

Germany

Number of animals: 20

Age at delivery: 5 weeks

Identification: Labeling by tattoo

Acclimatization: not less than 3 days

Husbandry:

Room number: EG-05, EG-06

Conditions: Optimum hygienic conditions, air-conditioned with 10 air changes per hour, and continually monitored environment with target ranges for temperature 22±2° C. and for relative humidity 45-65%, 12 hours artificial fluorescent lighting/12 hours darkness.

Accommodation:

max. 4 animals per individual ventilated cage (IVC, Zoonlab; Castrop-Rauxel, Germany; max. 4 mice/cage; cage size: 38×16×13 cm), at randomization mice assigned to the same group are housed together Diet:

M-Zucht (#V1126)

ssniff Spezialdiäten GmbH

Ferdinand-Gabriel-Weg 16

59494 Soest

Germany

Water: Community tap water (autoclaved)

Animal monitoring: Daily inspection and documentation of abnormalities

After the first treatment mice will be monitored for 30 minutes and then monitored 1 hour later. If any side effects are obvious, further hourly monitoring will take place up to 4 hours after therapy to evaluate any ethical abortion criteria.

Clinical signs: Daily inspection and documentation of abnormalities

Body weights: Three times weekly (generally Monday, Wednesday and Friday, can be shifted or reduced due to public holidays) after start of therapy Study update: Sponsor will receive a weekly study update.

If required for the welfare of the animals, observation and measurement frequencies might be increased.

Mice will be treated according to the following dosing schedule.

TABLE 1

| | | | Dose | | | | Number |
| | Test | Dose | Volume | Administration | Dosing | | of |
| Group | specimen | (nM/kg) | (ml/kg) | route | frequency | PK Regimen | animals |
|---|---|---|---|---|---|---|---|
| 1 | Vehicle | — | 5 | i.v. | Daily × 7 d | Necropsy on d 7, 2 hours after therapy | 4 |
| 2 | PDC_1 | 500 nM/kg | 5 | i.v. | Daily × 7 d | Necropsy on d 7, 2 hours after therapy | 4 |
| 3 | PDC_2 | 250 nM/kg | 5 | i.v. | Daily × 7 d | Necropsy on d 7, 2 hours after therapy | 4 |
| 4 | PDC_3 | 125 nM/kg | 5 | i.v. | Daily × 7 d | Necropsy on d 7, 2 hours after therapy | 4 |
| 5 | PDC_4 | 70 nM/kg | 5 | i.v. | Daily × 7 d | Necropsy on d 7, 2 hours after therapy | 4 |

Individual animals will be euthanized due to ethical abortion criteria prior study end without any necropsy. A final necropsy of the animals of all groups will be performed 2 h after therapy on Day 7 (see Table 1).

At final necropsy, animals will be weighed, and blood will be collected. Thereafter animals will be euthanized by cervical dislocation.

For blood collection, animals will be anaesthetized by isoflurane and blood will be taken with micro capillaries via retro-orbital vein puncture slightly rotated (terminal blood sampling, collection of ~400-500 µl full blood) and immediately transferred into EDTA coated tubes ($K_2E$ tubes) on ice. To obtain EDTA-plasma, tubes will be centrifuged at 4° C. for 10 min at 6800 g. After centrifugation, the supernatant will be transferred to a new polypropylene tube labeled with study and animal number (label is temperature-resistant –80 to +100° C., not adherent in liquid nitrogen) and stored at –80° C. until shipment. Test article and group/subset assignment will be documented in the allocation list, which will accompany the shipment.

All numerical data of this study will be graphically displayed in the final study report and additionally listed as tables in the attachment. Data of the individual groups will be analyzed using descriptive data analysis (Mean with SEM, Median with interquartile range). All data analysis will be performed using GraphPad Prism 5 from GraphPad Software, Inc., San Diego, USA.

Figure 8:
FIG. 8. Body weight change in mice upon administration of FNBPA5.1-MMAE conjugate (PDC) to non-tumor-bearing female BALB/c nude mice.
Figure 8:
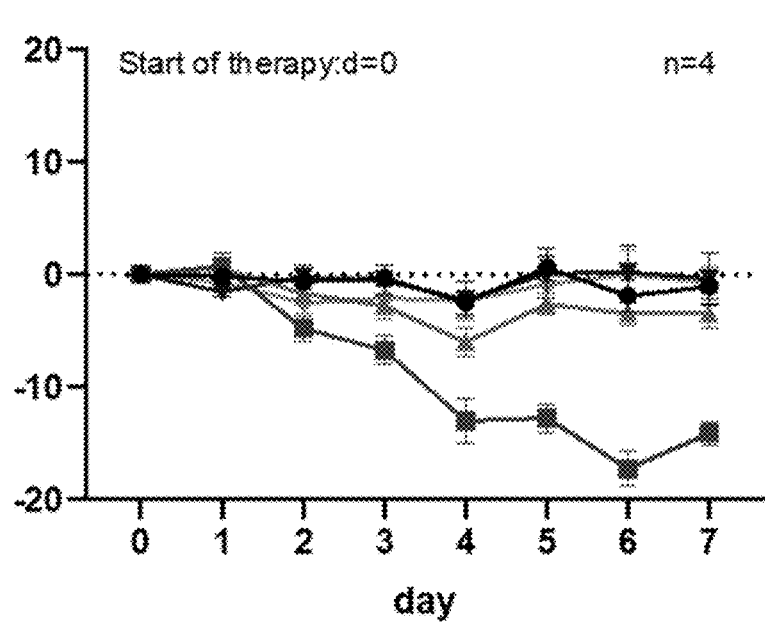

Results:

High concentration of PDC (500 nM/kg) was not tolerated well by the animals. All animals had a severe weight loss. For one animal (ID 05/22) the treatment was paused on Day 6 due to severe weight loss (>20%). On Day 7, the weight loss of all animals was <20%, so we were able to treat all mice before the final blood sampling (see FIG. 8).

Example 11—Peptide Drug Conjugate Efficacy Study Protocol

In this in vivo study, peptides toxin conjugate FNBPA5.1-MMAE (PDC) is evaluated for its efficacy in a xenograft tumor model of MDA-MB-231 (Z1) human breast cancer cells implanted into the mammary fat pad of female BALB/c nude mice.

Test Animals:

Species: *Mus musculus*

Strain: BALB/c nude (CAnN.Cg-Foxn1nu)

Sex: Female

Source: Charles River GmbH

Sandhofer Weg 7

97633 Sulzfeld

Germany

Number of animals: 20

Age at delivery: 5 weeks

Identification: Labeling by tattoo

Acclimatization: not less than 3 days

Cell culture:

Cell Line: MDA-MB-231 Z1_Luc

CPQ (PQ identifier): #234

Origin: Originated from human mammary carcinoma

Modification: Cell line was stably transfected with Luciferase cDNA, resulting in the MDA-MB-231_luc cell line expressing luciferase using a Hygromycin-resistance (3 mg/mL)

Incubation: 37° C., 10% $CO_2$

Medium: DMEM high Glutamax 1 with 10% FCS, 100 units penicillin/ml, and 100 µg of streptomycin/ml Expansion: 70%-90% confluent cultures are split routinely using trypsin/EDTA Quality control: Routine cell line authentication by a third party, as well as in-house mycoplasma testing using PCR Husbandry:

Room number: EG-05, EG-06

Conditions: Optimum hygienic conditions, air-conditioned with 10 air changes per hour, and continually monitored environment with target ranges for temperature 22±2° C. and for relative humidity 45-65%, 12 hours artificial fluorescent lighting/12 hours darkness.

Accommodation: max. 4 animals per individual ventilated cage (IVC, Zoonlab; Castrop-Rauxel, Germany; max. 4 mice/cage; cage size: 38×16×13 cm), at randomization mice assigned to the same group are housed together Diet: M-Zucht (#V1126)

ssniff Spezialdiäten GmbH

Ferdinand-Gabriel-Weg 16

59494 Soest

Germany

Water: Community tap water (autoclaved)

Tumor implantation:

On Day 0, MDA-MB-231 tumor cells ($5.0×10^6$ cells in 100 µl PBS) will be implanted into the left mammary fat pad of each mouse.

Animal monitoring: Daily inspection and documentation of abnormalities

Clinical signs: Daily inspection and documentation of abnormalities

Body weights: Three times weekly (generally Monday, Wednesday and Friday, can be shifted or reduced due to public holidays) after start of therapy Tumor growth monitoring: Two times weekly (generally Monday and Friday, can be shifted due to public holidays) after start of therapy: Primary tumor volumes will be determined by caliper measurement If required for the welfare of the animals, observation and measurement frequencies might be increased.

Primary tumor volumes will be determined by caliper measurement. Tumor sizes will be calculated according to the formula W2×L/2 (L=length and W=the perpendicular width of the tumor, L>W).

When a mean tumor volume of approx. 100-200 mm$^3$ is reached in a cohort of tumor-bearing mice, these tumor-bearing animals will be block-randomized. For block-randomization, a robust automated random number generation within individual blocks will be used (MS-Excel 2016).

Mice will be treated according to the following dosing schedule.

TABLE 2

|  |  |  | Dose Volume (ml/kg) | Administration route | Dosing frequency * | Number of animals |
|---|---|---|---|---|---|---|
| Group | Test specimen | Dose |  |  |  |  |
| 1 | Vehicle | — | 5 | i.v. | Daily for 7 days starting on day 1 | 8 |
| 2 | FNBPA5.1-MMAE | 250 nM/kg (1.232 mg/kg) | 5 | i.v. | Daily for 7 days starting on day 1 | 8 |

* d 0 = day of randomization

Individual animals will be euthanized due to ethical abortion criteria prior study end without any necropsy. A final necropsy of the animals of all groups will be performed as soon as the number of mice in any group is reduced by 30% (down to 6 animals) due to ethical abortion criteria.

All numerical data of this study will be graphically displayed in the final study report and additionally listed as tables in the attachment. Data of the individual groups will be analyzed using descriptive data analysis (Mean with SEM, Median with interquartile range. All data analysis will be performed using GraphPad Prism 5 from GraphPad Software, Inc., San Diego, USA.

Further examples and/or embodiments of the present invention are disclosed in the following numbered items.

1. A fibronectin binding peptide comprising the sequence:
FnI5BS-L1-FnI4BS-L2-FnI3BS-L3-FnI2BS
wherein:
FnI5BS is a polypeptide sequence selected from

```
                              (SEQ ID NO.: 1)
Gln-Val-Thr-Thr-Gly-Ser-Asn, (SEQ ID NO.: 2)
Gln-Val-Thr-Thr-Ala-Ser-Asn, (SEQ ID NO.: 3)
Gln-Val-Thr-Thr-Val-Ser-Asn,
```

-continued
and

```
                              (SEQ ID NO.: 4)
Gln-Val-Thr-Thr-Ser-Ser-Asn;
```

FnI4BS is a polypeptide sequence selected from

```
                              (SEQ ID NO.: 5)
Val-Glu-Phe-Thr-Glu-Glu-Ser, (SEQ ID NO.: 6)
Val-Glu-Phe-Ser-Glu-Glu-Ser, (SEQ ID NO.: 7)
Val-Glu-Phe-Cys-Glu-Glu-Ser, (SEQ ID NO.: 8)
Val-Glu-Phe-Asn-Glu-Glu-Ser,
and (SEQ ID NO.: 9)
Val-Glu-Phe-Gln-Glu-Glu-Ser;
```

FnI3BS is a polypeptide of sequence Gly-Ile-Val-Thr-Gly-Ala-Val (SEQ ID NO: 10);

FnI2BS is a polypeptide of sequence (His-Thr-Thr-Val-Glu-Asp-Thr (SEQ ID NO: 11); and L1, L2 and L3 are each a polypeptide sequence comprising 0, 1 or 2 amino acid residues.

2. The fibronectin binding peptide of item 1, wherein
FnI5BS is a polypeptide of sequence according to SEQ ID NO: 1; and/or
FnI4BS is a polypeptide of sequence according to SEQ ID NO: 5.

3. The fibronectin binding peptide of item 1 or 2, wherein
FnI5BS is a polypeptide of sequence according to SEQ ID NO: 1; and
FnI4BS is a polypeptide of sequence according to SEQ ID NO: 5.

4. The fibronectin binding peptide of any one of items 1 to 3, wherein
L1 is a single amino acid residue Leu; and/or
L2 is a single amino acid residue selected from Leu, Ile, Val, Ala and Met, preferably Leu; and/or
L3 is a dipeptide of sequence Ser-Asp.

5. The fibronectin binding peptide of any one of items 1 to 4, wherein
L1 is a single amino acid residue Leu; and
L2 is a single amino acid residue Leu; and
L3 is a dipeptide of sequence Ser-Asp.

6. The fibronectin binding peptide of any one of items 1 to 5, comprising a polypeptide sequence Gln-Val-Thr- Thr-Gly-Ser-Asn-Leu-Val-Glu-Phe-Thr-Glu-Glu-Ser-Leu-Gy-Ie-Val-Thr-Gly-Ala-Val-Ser-Asp-His-Thr-Thr-Val-Glu-Asp-Thr (SEQ ID NO: 12).

7. The fibronectin binding peptide of any one of items 1 to 6, having a polypeptide sequence according to SEQ ID NO: 12.

8. The fibronectin binding peptide of any one of items 1 to 7, characterized by binding to Fib1 (SEQ ID NO: 14) with a $K_D$ of 5.0 nM or tighter, as preferably determined by using a fluorescence polarization assay.

9. The fibronectin binding peptide of any one of items 1 to 8, further conjugated to a payload. wherein the payload is directly conjugated to the N or C terminus of the said polypeptide sequence through an amide bond, or wherein the payload is conjugated to the N or C terminus of the said polypeptide sequence via a linker.

10. The fibronectin binding peptide of any one of items 1 to 9, wherein the linker comprises a peptide moiety, a PEG moiety, a moiety derived from cadaverine or a $C_{1-12}$ alkylene moiety.

11. The fibronectin binding peptide of any one of items 1 to 10, wherein the payload is a biologically active molecule or an imaging agent.

12. The fibronectin binding peptide of item 11, wherein the payload is a biologically active molecule.

13. The fibronectin binding peptide of item 12, wherein the biologically active molecule is selected from the group consisting of cytostatic agent, cytotoxic agent, cytokine, transcription factor inhibitor, proteasome and protease inhibitor, apoptosis modulator, cell cycle modulator, angiogenesis inhibitor, hormone or hormone derivative, photodynamic therapy molecule, nano- and microparticle for thermoablation therapy, radionuclide, miRNA, siRNA and immunomodulatory antigen molecule, preferably wherein the cytostatic agent is selected from Doxorubicin, Paclitaxel, Chlorambucil, Topotecan and Vincristine;

preferably wherein the cytokine is selected from Interleukin-2, Interleukin-7, Interferon-γ and tumor necrosis factor;

preferably wherein the transcription factor inhibitor is selected from Curcumin, Ribavirin and Genistein;

preferably wherein the apoptosis modulator is selected from Imatinib, Erlotinib and Bryostatin; preferably wherein the cell cycle modulator is selected from Flavopiridol and Roscovitine; preferably wherein the angiogenesis inhibitor is selected from Endostatin, Celexocib, ADH-1 (exherin) and Sunitinib;

preferably wherein the hormone and hormone derivative is selected from Flutamide, Fosfestrol, Tamoxifen and Relaxin;

preferably wherein the radionuclide is selected from $^{68}$Ga, $^{64}$Cu, $^{90}$Y, $^{111}$In, $^{131}$I, $^{161}$Tb, $^{169}$Er and $^{177}$Lu;

preferably wherein the miRNA or the siRNAs is a miRNA or a siRNA specific for CD40, CD80 or CD86.

14. The fibronectin binding peptide of item 13, wherein the biologically active molecule is selected from the group consisting of Paclitaxel, Chlorambucil, Endostatin, Sunitinib, Interleukin-7, $^{177}$Lu, and $^{111}$In.

15. The fibronectin binding peptide of item 11, wherein the payload is an imaging agent.

16. The fibronectin binding peptide of item 15, wherein the imaging agent comprises a radionuclide, a fluorescent dye, a chemiluminescent agent, a bioluminescent agent, a spectrally resolvable inorganic fluorescent semiconductor nanocrystal, a metal nanoparticle, a nanocluster, a paramagnetic metal ion, an enzyme, a colorimetric label, biotin, dioxigenin, a hapten or a protein.

17. The fibronectin binding peptide of item 15, wherein the imaging agent is selected from the group consisting of radionuclide, MRI active compound, ultrasound contrast agent, fluorophore, marker for PET and SPECT, preferably selected from $^{44}$Sc, $^{64}$Cu, $^{67/68}$Ga $^{99m}$Tc, $^{111}$In, fluorophore in the far red/near-IR spectral region, and Gd-based and Fe-oxide particle based MRI contrast agent.

18. The fibronectin binding peptide of item 17, wherein the imaging agent is selected from $^{68}$Ga, $^{99m}$Tc, $^{111}$In, $^{44}$Sc and $^{64}$Cu.

19. The fibronectin binding peptide of any one of items 1 to 10, wherein the payload comprises a radionuclide, preferably selected from $^{67}$Cu, $^{90}$Y, $^{111}$In, $^{131}$I, $^{161}$Tb, $^{169}$Er and $^{177}$Lu or preferably selected from $^{44}$Sc, $^{64}$Cu, $^{67/68}$Ga $^{99}$Tc, and $^{111}$In.

20. The fibronectin binding peptide of any one of items 1 to 10, wherein the payload is [$^{111}$In]In-NODAGA moiety.

21. A pharmaceutical composition comprising the fibronectin binding peptide of any one of items 1 to 20 and a pharmaceutically acceptable carrier.

22. The fibronectin binding peptide of any one of items 1 to 14, 19 and 20 or the pharmaceutical composition of item 21 for use in therapy.

23. The fibronectin binding peptide of any one of items 1 to 14, 19 and 20 or the pharmaceutical composition of item 21 for use in the treatment or prevention of a disease associated with pathologic fibronectin accumulation.

24. The fibronectin binding peptide for use or the pharmaceutical composition for use of item 23, wherein the disease associated with pathologic fibronectin accumulation is selected from the group consisting of fibrosis, cancer, lymphedema, immune disease, autoimmune disease, and atherosclerosis.

25. The fibronectin binding peptide for use or the pharmaceutical composition for use of item 24, wherein the autoimmune diseases is selected from systemic sclerosis, diabetes type 1, Graves' disease, multiple sclerosis and rheumatoid arthritis.

26. The fibronectin binding peptide for use or the pharmaceutical composition for use of item 24, wherein the fibrosis is selected from pulmonary fibrosis, liver fibrosis, and kidney fibrosis.

27. The fibronectin binding peptide for use or the pharmaceutical composition for use of item 24, wherein the cancer is selected from breast cancer, head and neck squamous cell carcinoma, prostate cancer, renal cancer, pancreatic cancer and lung cancer.

28. The fibronectin binding peptide for use or the pharmaceutical composition for use of item 27, wherein the lung cancer is a non-small lung cell cancer.

29. The fibronectin binding peptide of any one of items 1 to 11 or 15 to 20 or the pharmaceutical composition of item 21 for use in diagnosis.

30. The fibronectin binding peptide of any one of items 1 to 11 or 15 to 20 or the pharmaceutical composition of item 21 for use in diagnosis of a disease associated with pathologic fibronectin accumulation.

31. The fibronectin binding peptide for use or the pharmaceutical composition for use of item 30, wherein the disease associated with pathologic fibronectin accumulation is selected from the group consisting of fibrosis, cancer, lymphedema, immune disease, autoimmune disease, and atherosclerosis.

32. The fibronectin binding peptide for use or the pharmaceutical composition for use of item 31, wherein the autoimmune diseases is selected from systemic sclerosis, diabetes type 1, Graves' disease, multiple sclerosis and rheumatoid arthritis.

33. The fibronectin binding peptide for use or the pharmaceutical composition for use of item 31, wherein the fibrosis is selected from pulmonary fibrosis, liver fibrosis, and kidney fibrosis.

34. The fibronectin binding peptide for use or the pharmaceutical composition for use of item 31, wherein the cancer is selected from breast cancer, head and neck squamous cell carcinoma, prostate cancer, renal cancer, pancreatic cancer and lung cancer.

35. The fibronectin binding peptide for use or the pharmaceutical composition for use of item 34, wherein the lung cancer is a non-small lung cell cancer.

---

The invention claimed is:

1. A fibronectin binding peptide comprising the sequence:
FnI5BS-L1-FnI4BS-L2-FnI3BS-L3-FnI2BS
wherein:
FnI5BS is a polypeptide sequence selected from

```
                                        (SEQ ID NO.: 1)
       Gln-Val-Thr-Thr-Gly-Ser-Asn, (SEQ ID NO.: 2)
       Gln-Val-Thr-Thr-Ala-Ser-Asn, (SEQ ID NO.: 3)
       Gln-Val-Thr-Thr-Val-Ser-Asn,
       and (SEQ ID NO.: 4)
       Gln-Val-Thr-Thr-Ser-Ser-Asn;
```

FnI4BS is a polypeptide sequence selected from

```
                                        (SEQ ID NO.: 5)
       Val-Glu-Phe-Thr-Glu-Glu-Ser, (SEQ ID NO.: 6)
       Val-Glu-Phe-Ser-Glu-Glu-Ser, (SEQ ID NO.: 7)
       Val-Glu-Phe-Cys-Glu-Glu-Ser, (SEQ ID NO.: 8)
       Val-Glu-Phe-Asn-Glu-Glu-Ser,
       and (SEQ ID NO.: 9)
       Val-Glu-Phe-Gln-Glu-Glu-Ser;
```

FnI3BS is a polypeptide of sequence Gly-Ile-Val-Thr-Gly-Ala-Val (SEQ ID NO.: 10);

FnI2BS is a polypeptide of sequence (His-Thr-Thr-Val-Glu-Asp-Thr (SEQ ID NO.: 11); and L1, L2 and L3 are each a polypeptide sequence comprising 0, 1 or 2 amino acid residues.

2. The fibronectin binding peptide of claim 1, wherein FnI5BS is a polypeptide of sequence according to SEQ ID NO.: 1; and/or FnI4BS is a polypeptide of sequence according to SEQ ID NO.: 5.

3. The fibronectin binding peptide of claim 1, wherein L1 is a single amino acid residue Leu; and/or L2 is a single amino acid residue selected from the group consisting of Leu, Ile, Val, Ala and Met; and/or L3 is a dipeptide of sequence Ser-Asp.

4. The fibronectin binding peptide of claim 1, wherein L1 is a single amino acid residue Leu; and L2 is a single amino acid residue Leu; and L3 is a dipeptide of sequence Ser-Asp.

5. The fibronectin binding peptide of claim 1, comprising a polypeptide sequence Gln-Val-Thr-Thr-Gly-Ser-Asn-Leu-Val-Glu-Phe-Thr-Glu-Glu-Ser-Leu-Gly-Ile-Val-Thr-Gly-Ala-Val-Ser-Asp-His-Thr-Thr-Val-Glu-Asp-Thr (SEQ ID NO: 12).

6. The fibronectin binding peptide of claim 1, characterized by binding to Fib1 (SEQ ID NO: 14) with a $K_D$ of 5.0 nM or tighter, as determined by using a fluorescence polarization assay.

7. The fibronectin binding peptide of claim 1, further conjugated to a payload, wherein the payload is directly conjugated to the N or C terminus of the said polypeptide sequence through an amide bond, or wherein the payload is conjugated to the N or C terminus of the polypeptide sequence via a linker.

8. The fibronectin binding peptide of claim 7, wherein the linker comprises a peptide moiety, a PEG moiety, a moiety derived from cadaverine or a $C_{1-12}$ alkylene moiety.

9. The fibronectin binding peptide of claim 7, wherein the payload is a biologically active molecule or an imaging agent.

10. The fibronectin binding peptide of claim 9, wherein the payload is a biologically active molecule.

11. The fibronectin binding peptide of claim 10, wherein the biologically active molecule is selected from the group consisting of cytostatic agent, cytotoxic agent, cytokine, transcription factor inhibitor, proteasome and protease inhibitor, apoptosis modulator, cell cycle modulator, angiogenesis inhibitor, hormone or hormone derivative, photodynamic therapy molecule, nano- and microparticle for thermoablation therapy, radionuclide, miRNA, siRNA and immunomodulatory antigen molecule.

12. The fibronectin binding peptide of claim 11, wherein the biologically active molecule is selected from the group consisting of Paclitaxel, Chlorambucil, Endostatin, Sunitinib, Interleukin-7, $^{177}$Lu, and $^{111}$In.

13. The fibronectin binding peptide of claim 9, wherein the payload is an imaging agent.

14. The fibronectin binding peptide of claim 13, wherein the imaging agent comprises a radionuclide, a fluorescent dye, a chemiluminescent agent, a bioluminescent agent, a spectrally resolvable inorganic fluorescent semiconductor nanocrystal, a metal nanoparticle, a nanocluster, a paramagnetic metal ion, an enzyme, a colorimetric label, biotin, dioxigenin, a hapten or a protein, or wherein the imaging agent is selected from the group consisting of radionuclide, MRI active compound, ultrasound contrast agent, fluorophore, marker for PET and SPECT.

15. The fibronectin binding peptide of claim 7, wherein the payload comprises a radionuclide, selected from the group consisting of $^{67}$Cu, $^{90}$Y, $^{111}$In, $^{131}$I, $^{161}$Tb, $^{169}$Er and $^{177}$Lu or selected from the group consisting of $^{44}$Sc, $^{64}$Cu, $^{67/68}$Ga $^{99}$Tc, and $^{111}$In, wherein the payload is [$^{111}$In]In-NODAGA moiety.

16. A pharmaceutical composition comprising the fibronectin binding peptide of claim 1 and a pharmaceutically acceptable carrier.

17. A method of treatment of a disease associated with pathologic fibronectin accumulation, the method comprising the step of administering the therapeutically effective amount of the fibronectin binding peptide of claim 10 to the subject in need thereof.

18. The method according to claim 17, wherein the disease associated with pathologic fibronectin accumulation is selected from the group consisting of fibrosis, cancer, lymphedema, immune disease, autoimmune disease, and atherosclerosis.

19. The method according to claim 18, wherein the disease associated with pathologic fibronectin accumulation is the autoimmune diseases, wherein the autoimmune disease is selected from systemic sclerosis, diabetes type 1, Graves' disease, multiple sclerosis and rheumatoid arthritis, or wherein the disease associated with pathologic fibronectin accumulation is the fibrosis, wherein the fibrosis is selected from pulmonary fibrosis, liver fibrosis, and kidney fibrosis, or wherein the disease associated with pathologic fibronectin accumulation is the cancer, wherein the cancer is selected from breast cancer, head and neck squamous cell carcinoma, prostate cancer, renal cancer, pancreatic cancer, and lung cancer.

20. A method of diagnosing a disease associated with pathologic fibronectin accumulation in a subject, the method comprising the step of administering the fibronectin-binding peptide of claim 13 to a subject and the step of detecting the pathologic fibronectin accumulation in said subject.

\* \* \* \* \*

SEQUENCE LISTING

```
Sequence total quantity: 17
SEQ ID NO: 1              moltype = AA  length = 7
FEATURE                   Location/Qualifiers
REGION                    1..7
                          note = FnI5 binding sequence with Gly at 5th position
source                    1..7
                          mol_type = protein
                          organism = synthetic construct
SEQUENCE: 1
QVTTGSN                                                              7

SEQ ID NO: 2              moltype = AA  length = 7
FEATURE                   Location/Qualifiers
REGION                    1..7
                          note = FnI5 binding sequence with Ala at 5th position
source                    1..7
                          mol_type = protein
                          organism = synthetic construct
SEQUENCE: 2
QVTTASN                                                              7

SEQ ID NO: 3              moltype = AA  length = 7
FEATURE                   Location/Qualifiers
REGION                    1..7
                          note = FnI5 binding sequence with Val at 5th position
source                    1..7
                          mol_type = protein
                          organism = synthetic construct
SEQUENCE: 3
QVTTVSN                                                              7

SEQ ID NO: 4              moltype = AA  length = 7
FEATURE                   Location/Qualifiers
REGION                    1..7
                          note = FnI5 binding sequence with Ser at 5th position
source                    1..7
                          mol_type = protein
                          organism = synthetic construct
SEQUENCE: 4
QVTTSSN                                                              7

SEQ ID NO: 5              moltype = AA  length = 7
FEATURE                   Location/Qualifiers
REGION                    1..7
                          note = FnI4 binding sequence with Thr at 4th position
source                    1..7
                          mol_type = protein
                          organism = synthetic construct
SEQUENCE: 5
VEFTEES                                                              7

SEQ ID NO: 6              moltype = AA  length = 7
FEATURE                   Location/Qualifiers
REGION                    1..7
                          note = FnI4 binding sequence with Ser at 4th position
source                    1..7
                          mol_type = protein
                          organism = synthetic construct
SEQUENCE: 6
VEFSEES                                                              7

SEQ ID NO: 7              moltype = AA  length = 7
```

-continued

```
FEATURE              Location/Qualifiers
REGION               1..7
                     note = FnI4 binding sequence with Cys at 4th position
source               1..7
                     mol_type = protein
                     organism = synthetic construct
SEQUENCE: 7
VEFCEES                                                                  7

SEQ ID NO: 8         moltype = AA   length = 7
FEATURE              Location/Qualifiers
REGION               1..7
                     note = FnI4 binding sequence with Asn at 4th position
source               1..7
                     mol_type = protein
                     organism = synthetic construct
SEQUENCE: 8
VEFNEES                                                                  7

SEQ ID NO: 9         moltype = AA   length = 7
FEATURE              Location/Qualifiers
REGION               1..7
                     note = FnI4 binding sequence with Gln at 4th position
source               1..7
                     mol_type = protein
                     organism = synthetic construct
SEQUENCE: 9
VEFQEES                                                                  7

SEQ ID NO: 10        moltype = AA   length = 7
FEATURE              Location/Qualifiers
REGION               1..7
                     note = FnI3 binding sequence
source               1..7
                     mol_type = protein
                     organism = synthetic construct
SEQUENCE: 10
GIVTGAV                                                                  7

SEQ ID NO: 11        moltype = AA   length = 7
FEATURE              Location/Qualifiers
REGION               1..7
                     note = FnI2 binding sequence
source               1..7
                     mol_type = protein
                     organism = synthetic construct
SEQUENCE: 11
HTTVEDT                                                                  7

SEQ ID NO: 12        moltype = AA   length = 32
FEATURE              Location/Qualifiers
REGION               1..32
                     note = FnBPA5.1
source               1..32
                     mol_type = protein
                     organism = synthetic construct
SEQUENCE: 12
QVTTGSNLVE FTEESLGIVT GAVSDHTTVE DT                                     32

SEQ ID NO: 13        moltype = AA   length = 34
FEATURE              Location/Qualifiers
REGION               1..34
                     note = FnBPA5
source               1..34
                     mol_type = protein
                     organism = synthetic construct
SEQUENCE: 13
QVTTESNLVE FDEESTKGIV TGAVSDHTTV EDTK                                   34

SEQ ID NO: 14        moltype = AA   length = 290
FEATURE              Location/Qualifiers
REGION               1..290
                     note = Fib1
source               1..290
                     mol_type = protein
                     organism = synthetic construct
SEQUENCE: 14
MLRGPGPGLL LLAQVCLGTA VPSTGASKSK RQAQQMVQPQ SPVAVSQSKP GCYDNGKHYQ  60
INQQWERTYL GNALVCTCYG GSRGFNCESK PEAEETCFDK YTGNTYRVGD TYERPKDSMI  120
```

-continued

```
WDCTCIGAGR GRISCTIANR CHEGGQSYKI GDTWRRPHET GGYMLECVCL GNGKGEWTCK  180
PIAEKCFDHA AGTSYVVGET WEKPYQGWMM VDCTCLGEGS GRITCTSRNR CNDQDTRTSY  240
RIGDTWSKKD NRGNLLQCIC TGNGRGEWKC ERHTSVQTTS SGSGPFTDVR             290

SEQ ID NO: 15          moltype = AA   length = 4
FEATURE                Location/Qualifiers
REGION                 1..4
                       note = Cys-Gly-Gly-Gly linker
source                 1..4
                       mol_type = protein
                       organism = synthetic construct
SEQUENCE: 15
CGGG                                                                4

SEQ ID NO: 16          moltype = AA   length = 36
FEATURE                Location/Qualifiers
REGION                 1..36
                       note = NODAGA-FnBPA5.1
MOD_RES                1
                       note = X at position 1 is Ac-Cys(Mal-NODAGA)
source                 1..36
                       mol_type = protein
                       organism = synthetic construct
SEQUENCE: 16
XGGGQVTTGS NLVEFTEESL GIVTGAVSDH TTVEDT                              36

SEQ ID NO: 17          moltype = AA   length = 36
FEATURE                Location/Qualifiers
REGION                 1..36
                       note = Cy5-FnBPA5.1
MOD_RES                1
                       note = X at position 1 is Cys(Mal-Cy5)
source                 1..36
                       mol_type = protein
                       organism = synthetic construct
SEQUENCE: 17
XGGGQVTTGS NLVEFTEESL GIVTGAVSDH TTVEDT                              36
```